(12) United States Patent
Oren et al.

(10) Patent No.: US 11,166,711 B2
(45) Date of Patent: *Nov. 9, 2021

(54) JOINING DEVICES, KITS AND METHODS

(71) Applicant: ARCURO MEDICAL LTD., M.P. Misgav (IL)

(72) Inventors: Ran Oren, Kibbutz Gaaton (IL); Lee Ranon, Shavei Zion (IL); Elad Rash, Bethlehem of Galilee (IL)

(73) Assignee: ARCURO MEDICAL LTD., M.P. Misgav (IL)

( * ) Notice: Subject to any disclaimer, the term of this patent is extended or adjusted under 35 U.S.C. 154(b) by 274 days.

This patent is subject to a terminal disclaimer.

(21) Appl. No.: 16/113,732

(22) Filed: Aug. 27, 2018

(65) Prior Publication Data

US 2018/0360441 A1    Dec. 20, 2018

Related U.S. Application Data

(63) Continuation of application No. 14/907,847, filed as application No. PCT/IL2014/050692 on Jul. 30, 2014, now Pat. No. 10,058,320.

(Continued)

(51) Int. Cl.
*A61B 17/04* (2006.01)
*A61B 17/06* (2006.01)

(52) U.S. Cl.
CPC .. *A61B 17/0401* (2013.01); *A61B 2017/0406* (2013.01); *A61B 2017/0409* (2013.01); *A61B 2017/0414* (2013.01); *A61B 2017/0417* (2013.01); *A61B 2017/0458* (2013.01); *A61B 2017/0462* (2013.01);

(Continued)

(58) Field of Classification Search
CPC ............ A61B 17/0466; A61B 17/0401; A61B 2017/0406; A61B 2017/0409; A61B 2017/0414; A61B 2017/0417; A61B 2017/0458; A61B 2017/0462; A61B 2017/0464; A61B 2017/0472; A61B 2017/06042; A61B 2017/06176; A61B 2017/06185; A61B 17/0487;
(Continued)

(56) References Cited

U.S. PATENT DOCUMENTS

| 5,584,836 A | 12/1996 | Ballintyn |
| 8,163,022 B2 * | 4/2012 | Bentley .............. A61B 17/0057 623/17.11 |

(Continued)

FOREIGN PATENT DOCUMENTS

| WO | 2010045179 A1 | 4/2010 |
| WO | 2012096706 A1 | 7/2012 |

*Primary Examiner* — Melanie R Tyson
*Assistant Examiner* — Uyen N Vo
(74) *Attorney, Agent, or Firm* — The Roy Gross Law Firm, LLC; Roy Gross

(57) ABSTRACT

A device comprising: a flexible tube comprising a first collapsible end portion; a first actuating element segment secured to the first collapsible end portion and extending along the first collapsible end portion, wherein, when the first collapsible end portion is threaded through a first aperture and the first actuating element segment is pulled proximally, the first collapsible end portion collapses proximally and forms a bulge larger than the first aperture, thereby anchoring the flexible tube against a rim of the first aperture.

6 Claims, 18 Drawing Sheets

Related U.S. Application Data

(60) Provisional application No. 61/859,865, filed on Jul. 30, 2013.

(52) U.S. Cl.
CPC ............... *A61B 2017/0464* (2013.01); *A61B 2017/0472* (2013.01); *A61B 2017/06042* (2013.01); *A61B 2017/06176* (2013.01); *A61B 2017/06185* (2013.01)

(58) Field of Classification Search
CPC ..... A61B 2017/0446; A61B 2017/0496; A61F 2/0811; A61F 2/0817
See application file for complete search history.

(56) References Cited

U.S. PATENT DOCUMENTS

| | | |
|---|---|---|
| 2002/0019649 A1 | 2/2002 | Sikora et al. |
| 2004/0122456 A1 | 6/2004 | Saadat et al. |
| 2005/0033363 A1 | 2/2005 | Bojarski et al. |
| 2005/0125035 A1 | 6/2005 | Cichocki, Jr. et al. |
| 2005/0277966 A1* | 12/2005 | Ewers ............... A61B 17/0401 606/153 |
| 2006/0190042 A1 | 8/2006 | Stone et al. |
| 2006/0259074 A1 | 11/2006 | Kelleher et al. |
| 2007/0010857 A1 | 1/2007 | Sugimoto et al. |
| 2007/0185532 A1* | 8/2007 | Stone ............... A61B 17/0469 606/232 |
| 2007/0203391 A1 | 8/2007 | Bloom et al. |
| 2008/0009888 A1 | 1/2008 | Ewers et al. |
| 2008/0140092 A1 | 6/2008 | Stone et al. |
| 2009/0306711 A1* | 12/2009 | Stone ............... A61B 17/0469 606/232 |
| 2010/0023048 A1 | 1/2010 | Mach |
| 2010/0087857 A1 | 4/2010 | Stone et al. |
| 2010/0094425 A1 | 4/2010 | Bentley et al. |
| 2011/0022061 A1 | 1/2011 | Orphanos et al. |
| 2011/0022084 A1 | 1/2011 | Sengun et al. |
| 2011/0087284 A1 | 4/2011 | Stone et al. |
| 2011/0098727 A1 | 4/2011 | Kaiser et al. |
| 2012/0239085 A1 | 9/2012 | Schlotterback et al. |
| 2013/0123810 A1* | 5/2013 | Brown ............... A61B 17/0401 606/144 |
| 2013/0226234 A1* | 8/2013 | Avelar ............... D04C 1/12 606/231 |
| 2014/0074160 A1* | 3/2014 | Denham ............. A61B 17/0401 606/232 |
| 2014/0249577 A1* | 9/2014 | Pilgeram ............ A61B 17/0485 606/228 |

* cited by examiner

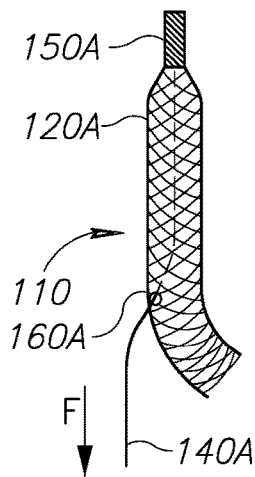 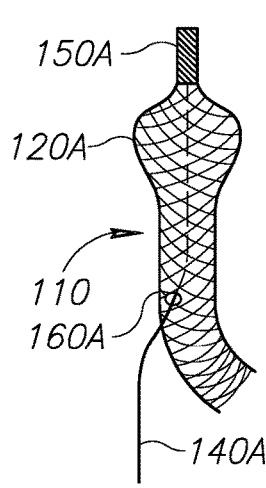 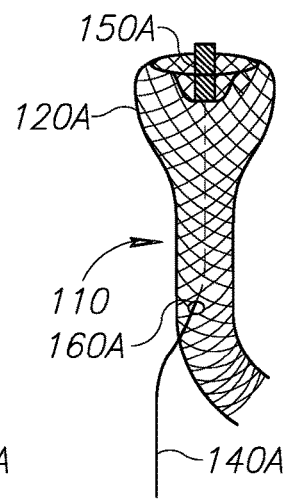 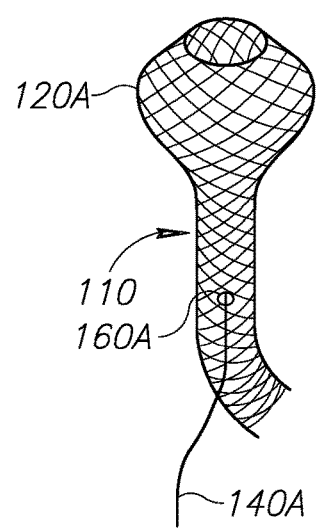
FIG.3A    FIG.3B    FIG.3C    FIG.3D
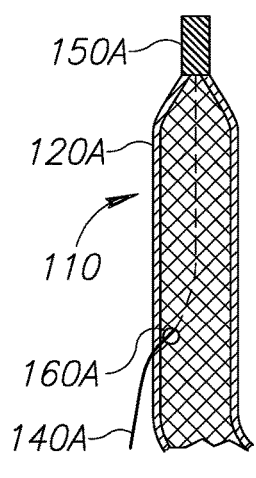 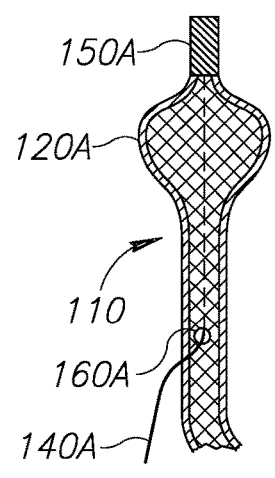 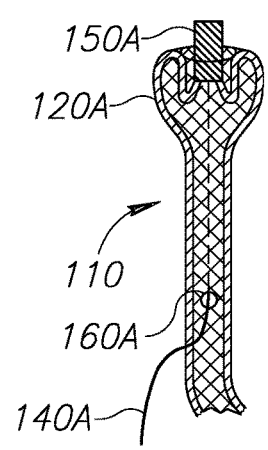 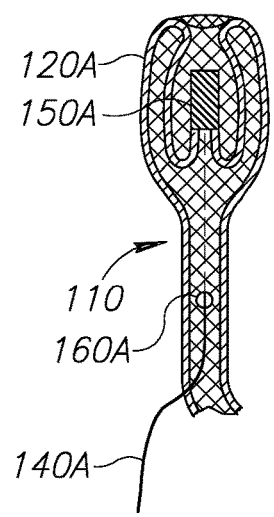
FIG.4A    FIG.4B    FIG.4C    FIG.4D

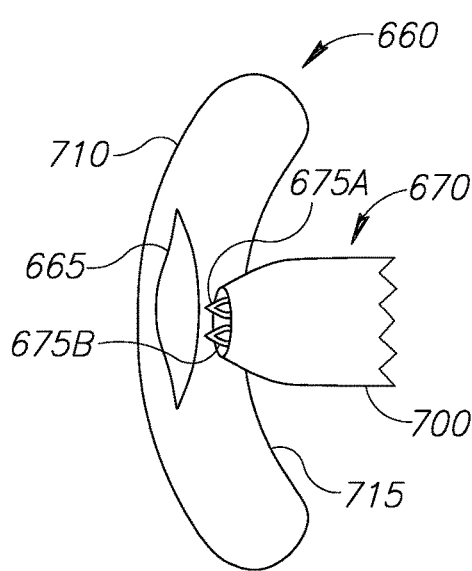
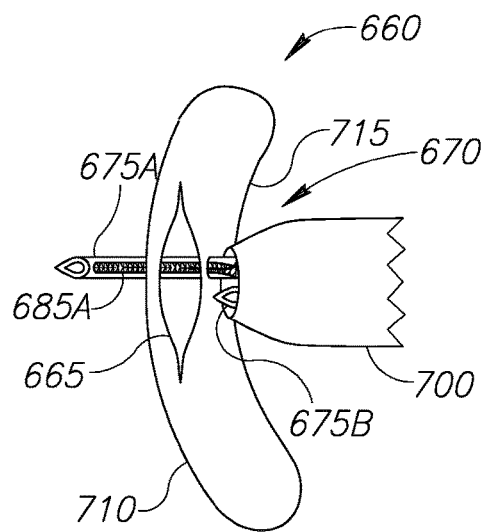
FIG.14A  FIG.14B
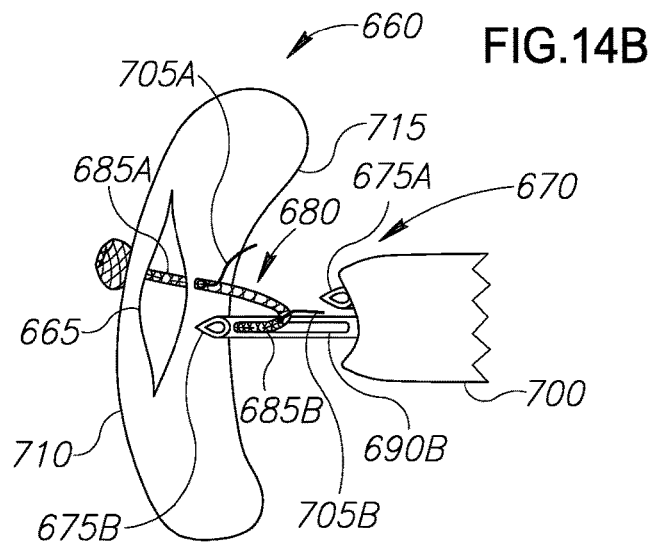
FIG.14C
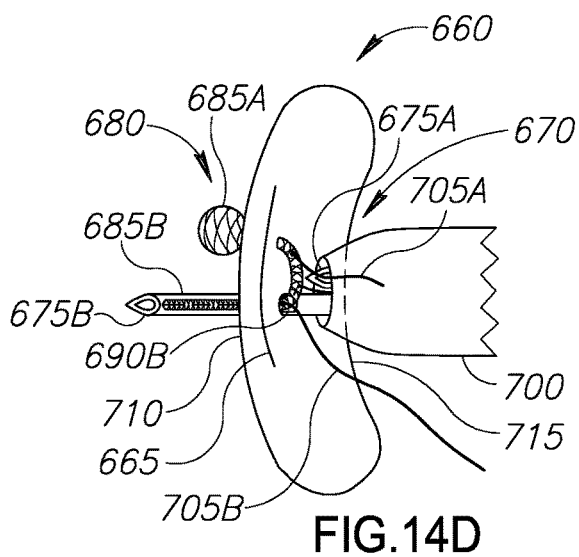
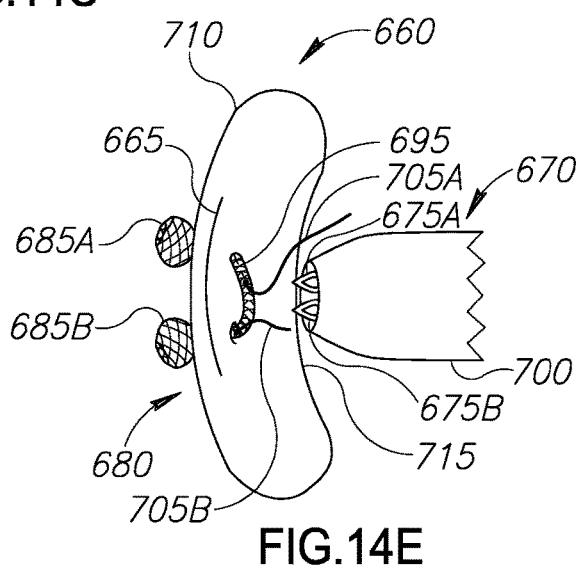
FIG.14D  FIG.14E

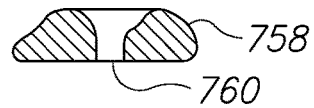
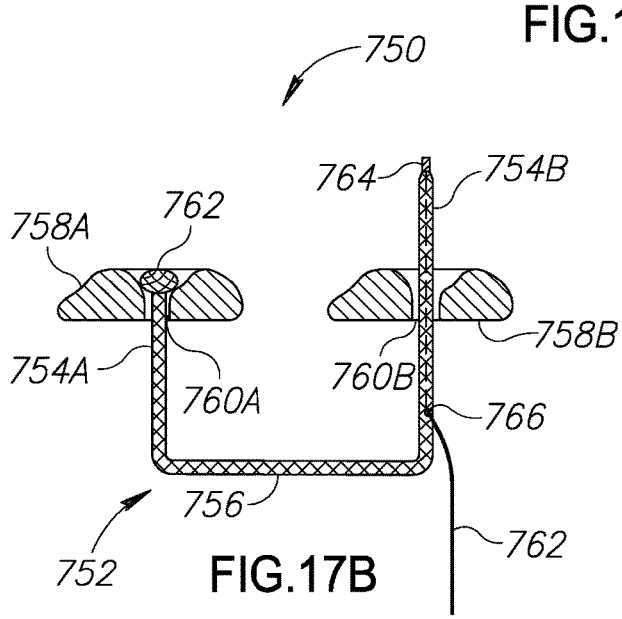
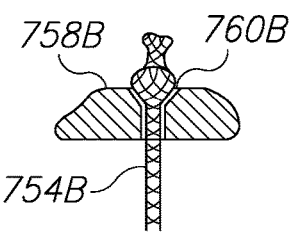
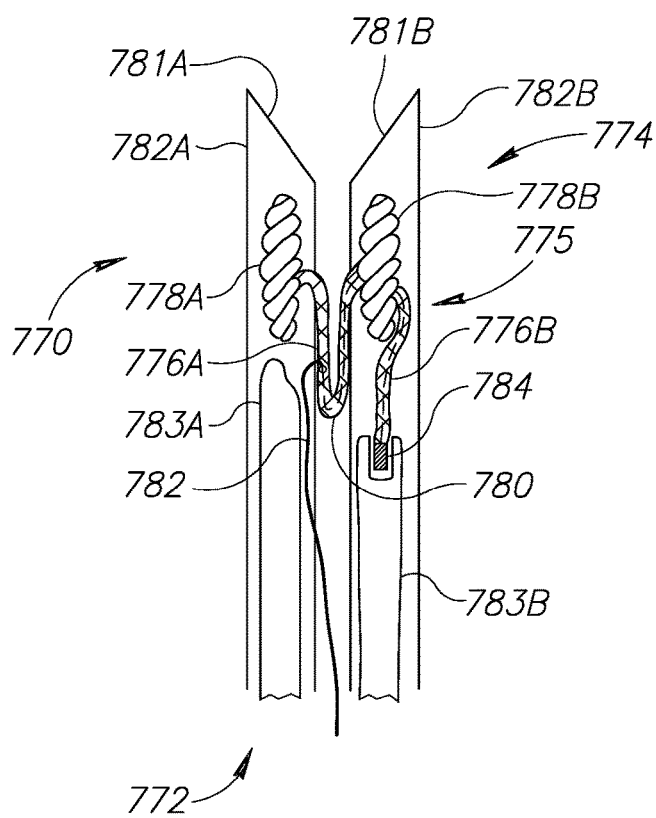
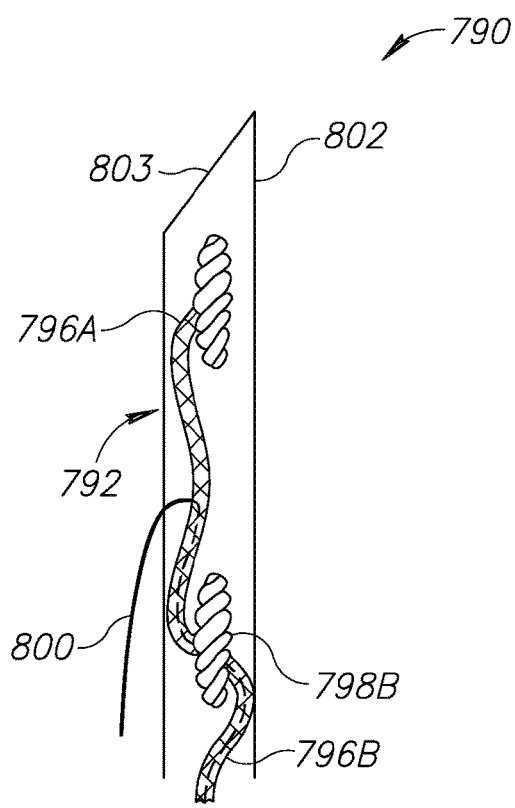
FIG.17A
FIG.17B
FIG.17C
FIG.18A
FIG.18B

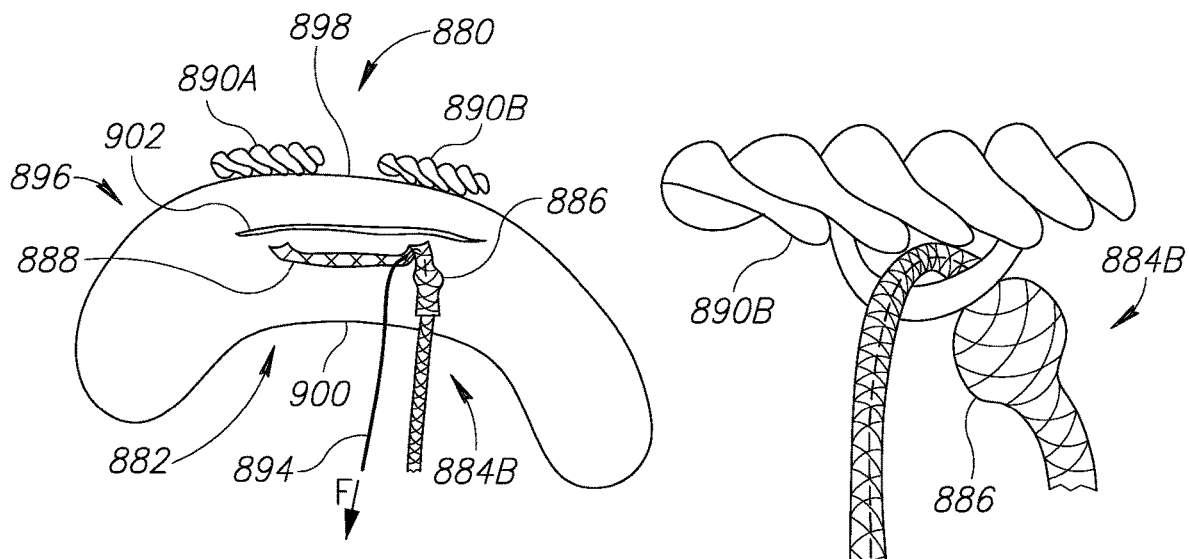
FIG.23C
FIG.23D
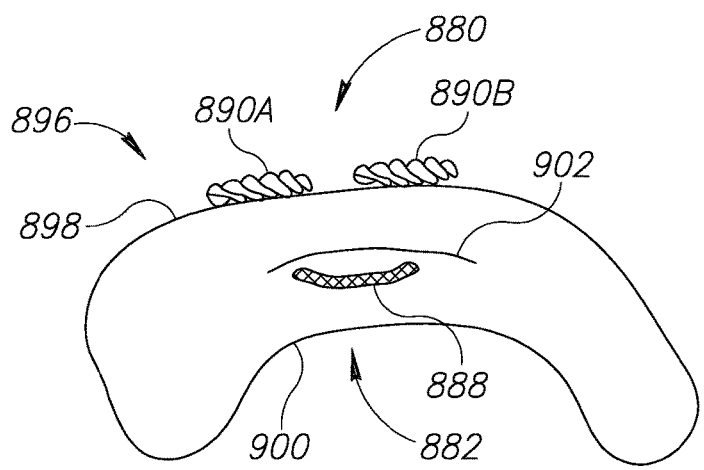
FIG.23E

JOINING DEVICES, KITS AND METHODS

CROSS REFERENCE TO RELATED APPLICATIONS

This application is a Continuation of U.S. patent application Ser. No. 14/907,847 filed on Jan. 27, 2016 which is a 371 of International Patent Application No. PCT/IL2014/050692 filed on Jul. 30, 2014, which claims the benefit of priority of U.S. Provisional Patent Application No. 61/859,865, filed on Jul. 30, 2013. The contents of the above applications are all hereby expressly incorporated by reference, in their entirety.

BACKGROUND

In humans, the two knee menisci reside between the thigh bone femur and the shin bone tibia. While the ends of the thigh bone and the shin bone have a thin covering of soft hyaline cartilage, the menisci are made of tough fibrocartilage and conform to the surfaces of the bones they rest on. One meniscus rest on the medial tibial plateau; this is the medial meniscus. The other meniscus rests on the lateral tibial plateau; this is the lateral meniscus.

These menisci act to distribute body weight across the knee joint. Without the menisci, the weight of the body would be unevenly applied to the femur and tibia. This uneven weight distribution would cause the development of abnormal excessive forces leading to early damage of the knee joint. The menisci also contribute to the stability of the joint.

The menisci are nourished by small blood vessels but have a large area in the center with no direct blood supply. This presents a problem when there is an injury to the meniscus, as the avascular areas tend not to heal. Without the essential nutrients supplied by blood vessels, healing cannot take place.

The two most common causes of a meniscal tear are traumatic injury and degenerative processes, which are the most common tear seen in all ages of patients. Meniscal tears can occur in all age groups. Traumatic tears are most common in active people aged 10-45. Traumatic tears are usually radial or vertical in the meniscus and more likely to produce a moveable fragment that can catch in the knee and therefore require surgical treatment.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a device comprising: a flexible tube comprising a first collapsible end portion; a first actuating element segment secured to the first collapsible end portion and extending along the first collapsible end portion, wherein, when the first collapsible end portion is threaded through a first aperture and the first actuating element segment is pulled proximally, the first collapsible end portion collapses proximally and forms a bulge larger than the first aperture, thereby anchoring the flexible tube against a rim of the first aperture.

In some embodiments, the flexible tube further comprises a second collapsible end portion, and the device further comprises a second actuating element segment secured to the second collapsible end portion and extending along the second collapsible end portion, wherein, when the first and second collapsible end portions are threaded through the first aperture and a second aperture, respectively, and the first and second actuating element segments are pulled proximally, each of the first and second collapsible end portions collapses proximally and forms a bulge larger than a respective one of the first and second apertures, thereby anchoring the flexible tube against a rim of a respective one of the first and second apertures.

In some embodiments, an end portion of each of the first and second actuating element segments is located externally to the flexible tube.

In some embodiments, each of the first and the second actuating element segments extends along an inner void of a respective one of the first and second collapsible end portions and wherein each of the first and second collapsible end portions collapses into the inner void of the respective one of the first and second collapsible end portions.

In some embodiments, each of the first and second actuating element segments is threaded laterally and repeatedly through a respective one of the first and second collapsible end portions, and wherein the first and second actuating element segments are pulled proximally, each of the first and second collapsible end portions folds laterally and repeatedly on itself.

In some embodiments, each of the first and second collapsible end portions comprises a hardened portion located along a respective one of the first and second collapsible end portions at a predefined distance from a tip of the respective one of the first and second collapsible end portions, and wherein when the first and second actuating element segments are pulled proximally: each of the first and second collapsible end portions collapses into a section of an inner void of a respective one of the first and second collapsible end portions formed between the tip and the hardened portion of the respective one of the first and second collapsible end portions, and the hardened portion of each of the first and second collapsible end portions collapses into the remainder of the inner void of the respective one of the first and second collapsible end portions.

In some embodiments, each of the first and second collapsible end portions comprises a hardened tip, the first actuating element segment is secured to the hardened tip of the first collapsible end portion, and the second actuating element segment is secured to the hardened tip of the second collapsible end portion.

In some embodiments, the hardened tip of each of the first and second collapsible end portions comprises barbs, and wherein the barbs are configured to secure each hardened tip to a respective one of the first and second collapsible end portions when it is collapsed.

In some embodiments, the device further comprises a first actuating element comprising the first actuating element segment and a second actuating element comprising the second actuating element segment.

In some embodiments, the first and second end portions are a tubular mesh.

In some embodiments, the first and second actuating element segment selected from a group consisting of: a thread and a rigid roll.

There is further provided, in accordance with an embodiment, a device comprising a flexible tube, the flexible tube comprising: an end portion comprising a first elongated hardened element located at a tip of the end portion; a collapsible end portion comprising a second elongated hardened element threaded thereon; and an actuating element secured to the collapsible end portion, wherein, when the end portion and the collapsible end portion are threaded through two apertures, respectively, and the actuating element is pulled proximally, the collapsible end portion collapses proximally and forms a bulge in vicinity to the second elongated hardened element, and wherein: a length dimension of the first elongated hardened element is larger than a respective one of the two apertures, the bulge and a length dimension of the second elongated hardened element are larger than a respective one of the two apertures, thereby anchoring the flexible tube against a rim of each of the two apertures.

In some embodiments, each of the first and second elongated hardened elements has an involute shape.

In some embodiments, the first elongated hardened element and the second elongated hardened element are made of polymer.

In some embodiments, the collapsible end portion comprises a hardened tip and the actuating element is secured to the hardened tip.

In some embodiments, the collapsible end portion is a tubular mesh.

In some embodiments, the actuating element is selected from a group consisting of a thread and a rigid roll.

There is further provided, in accordance with an embodiment, a device comprising: a flexible tube comprising: a first end portion comprising a first elongated hardened element located at a tip of the end portion; a second end portion comprising: a second elongated hardened element threaded thereon, a pulling anchor located along the second end portion, and a collapsible segment extending from the pulling anchor towards a middle portion of the flexible tube; and an actuating element secured to the pulling anchor and extending along the second end portion towards the middle portion of the flexible tube; wherein, when: the first end portion is threaded through a first aperture smaller than a length dimension of the first elongated hardened element, and the second end portion is threaded back and forth, at least once, through a second aperture smaller than a length dimension of the second elongated hardened element, and such that the second elongated hardened element and the pulling anchor are located at different sides with respect to the second aperture, the actuating element is pulled proximally, wherein the collapsible segment of the second end portion collapses towards the second elongated hardened element and forms a bulge larger than the second aperture, thereby anchoring the flexible tube against a rim of the first aperture and two rims at two sides of the second aperture.

In some embodiments, each of the first and second elongated hardened elements has an involute shape.

In some embodiments, each of the first and second elongated hardened elements is made of polymer.

There is further provided, in accordance with an embodiment, a device for repairing a tear in a meniscus tissue, the device comprising: a flexible tube comprising two collapsible end portions; a first actuating element segment secured to the first collapsible end portion and extending along the first collapsible end portion; and a second actuating element segment secured to the second collapsible end portion and extending along the second collapsible end portion, wherein, when the first and second collapsible end portions are threaded through two apertures made in the meniscus tissue through the tear, and the first and second actuating element segments are pulled proximally, the first and second collapsible end portions each collapses proximally and forms a bulge larger than a respective one of the two apertures, thereby anchoring the flexible tube against a peripheral distal wall of the meniscus tissue.

In some embodiments, each actuating element segment of the first and second actuating element segments exits the flexible tube through a middle portion of the flexible tube.

In some embodiments, each one of the first and second actuating element segments extends along an inner void of the respective one of the first and second collapsible end portions and wherein each one of the first and second collapsible end portions collapses into its inner void.

In some embodiments, each actuating element segment of the first and second actuating element segments is threaded laterally and repeatedly through the respective one of the first and second collapsible end portions, and wherein when the first and second actuating element segments are pulled proximally, each one of the first and second collapsible end portions folds laterally and repeatedly on itself In some embodiments, each of the first and second collapsible end portions comprises a hardened portion located along a respective one of the first and second collapsible end portions at a predefined distance from a tip of the respective one of the first and second collapsible end portions, and wherein when the first and second actuating element segments are pulled proximally: each of the first and second collapsible end portions collapses into a section of an inner void of a respective one of the first and second collapsible end portions formed between the respective tip and the respective hardened portion, and the hardened portion of each of the first and second collapsible end portions collapses into a remainder of the respective inner void.

In some embodiments: each of the first and second collapsible end portions comprises a hardened tip, the first actuating element segment is secured to the hardened tip of the first collapsible end portion, and the second actuating element segment is secured to the hardened tip of the second collapsible end portion.

In some embodiments, the hardened tip of each of the first and second collapsible end portions comprises barbs, and wherein the barbs are configured to secure each hardened tip to each respective one of the first and second collapsible end portions when it is collapsed.

In some embodiments, the device further comprises a first actuating element comprising the first actuating element segment and a second actuating element comprising the second actuating element segment.

In some embodiments, the first and second end portions are a tubular mesh.

In some embodiments, the first and second actuating element segment selected from a group consisting of: a thread and a rigid roll.

There is further provided, in accordance with an embodiment, a device for repairing a tear in a meniscus tissue, the device comprising: a flexible tube comprising: an end portion comprising a first elongated hardened element located at a tip of the end portion, a collapsible end portion comprising a second elongated hardened element threaded thereon, and an actuating element secured to the collapsible end portion, wherein, when: the end portion and the collapsible end portion are threaded through two apertures, respectively, wherein the two apertures are made in the meniscus tissue and through the tear, and the actuating element is pulled proximally, the second collapsible end portion collapses proximally and forms a bulge in vicinity to the second elongated hardened element, and wherein: a length dimension of the first elongated hardened element is larger than a respective one of the two apertures, and the bulge and a length dimension of the second elongated hardened element are larger than a respective one of the two apertures, thereby anchoring the flexible tube against a peripheral distal wall of the meniscus tissue.

In some embodiments, each of the first and second elongated hardened elements has an involute shape.

In some embodiments, each of the first and second elongated hardened elements are made of polymer.

In some embodiments, the collapsible end portion comprises a hardened tip and the actuating element is secured to the hardened tip.

In some embodiments, the collapsible end portion is a tubular mesh.

In some embodiments, the actuating element is selected from a group consisting of: a thread and a rigid roll.

There is further provided, in accordance with an embodiment, a device for repairing a tear in a meniscus tissue, the device comprising: a flexible tube comprising: a first end portion comprising a first elongated hardened element located at a tip of the first end portion; a second end portion comprising: a second elongated hardened element threaded thereon, a pulling anchor located along the second end portion, and a collapsible segment extending from the pulling anchor towards a middle portion of the flexible tube; and an actuating element secured to the pulling anchor and extending along the second end portion towards the middle portion of the flexible tube; wherein, when: the first end portion is threaded through a first aperture smaller than a length dimension of the first elongated hardened element, and the second end portion is threaded back and forth through a second aperture, smaller than a length dimension of the second elongated hardened element, and such that the second elongated hardened element and the pulling anchor are located at different sides with respect to the second aperture, and wherein the first aperture and the second aperture are made in the meniscus tissue through the tear, the actuating element is pulled proximally, wherein the collapsible segment of the second end portion collapses towards the second elongated hardened element and forms a bulge larger than the second aperture, thereby anchoring the flexible tube to the meniscus tissue.

In some embodiments, each of the first and second elongated hardened elements has an involute shape.

In some embodiments, each of the first and second elongated hardened elements are made of polymer.

In some embodiments, the second end portion is a tubular mesh.

In some embodiments, the actuating element is selected from a group consisting of: a thread and a rigid roll.

There is further provided, in accordance with an embodiment, a kit for repairing a tear in a meniscus tissue, the kit comprising: an implant comprising: a flexible tube comprising two collapsible end portions, a first actuating element segment secured to the first collapsible end portion and extending along the first collapsible end portion, and a second actuating element segment secured to the second collapsible end portion and extending along the second collapsible end portion; and an applicator configured to deploy the implant in the meniscus tissue by puncturing the meniscus tissue to form two apertures passing through the tear and threading the first and second collapsible end portions through the two apertures; wherein, when: the first and second collapsible end portions are threaded through the meniscus tissue, and the first and second actuating element segments are pulled proximally, the first and second collapsible end portions each collapses proximally and forms a bulge larger than a respective one of the two apertures, thereby anchoring the implant against a peripheral distal wall of the meniscus tissue.

In some embodiments, each actuating element segment of the first and second actuating element segments exits the flexible tube through a middle portion of the flexible tube.

In some embodiments, each one of the first and second actuating element segments extends along an inner void of the respective one of the first and second collapsible end portions and wherein each one of the first and second collapsible end portions collapses into its inner void.

In some embodiments, each actuating element segment of the first and second actuating element segments is threaded laterally and repeatedly through the respective one of the first and second collapsible end portions, and wherein when the first and second actuating element segments are pulled proximally, each one of the first and second collapsible end portions folds laterally and repeatedly on itself In some embodiments, each of the first and second collapsible end portions comprises a hardened portion located along a respective one of the first and second collapsible end portions at a predefined distance from a tip of the respective one of the first and second collapsible end portions, and wherein when the first and second actuating element segments are pulled proximally: each of the first and second collapsible end portions collapses into a section of an inner void of a respective one of the first and second collapsible end portions formed between the respective tip and the respective hardened portion, and the hardened portion of each of the first and second collapsible end portions collapses into a remainder of the respective inner void.

In some embodiments: each of the first and second collapsible end portions comprises a hardened tip, the first actuating element segment is secured to the hardened tip of the first collapsible end portion, and the second actuating element segment is secured to the hardened tip of the second collapsible end portion.

In some embodiments, the hardened tip of each of the first and second collapsible end portions comprises barbs, and wherein the barbs are configured to secure each hardened tip to a respective one of the first and second collapsible end portions when it is collapsed.

In some embodiments, the kit further comprises a first actuating element comprising the first actuating element segment and a second actuating element comprising the second actuating element segment.

In some embodiments, the applicator comprises: a first and a second tubular needles, wherein each one of the first and second tubular needles is configured to puncture the meniscus tissue to form a respective one of the two apertures, and wherein each one of the first and second tubular needles comprises: an opening configured to allow insertion of a tip of a respective one of the first and second collapsible end portions into a respective one of the first and second tubular needles, and a rod positioned there within and configured to maintain the tip of the respective one of the first and second collapsible end portions in place within the respective one of the first and second tubular needles.

In some embodiments, the applicator comprises: a tubular needle configured to puncture the meniscus tissue to form the two apertures, wherein the tubular needle comprises a first and a second openings, each configured to allow insertion of a tip of a respective one of the first and second collapsible end portions into the tubular needle, and a first and a second rod positioned within the tubular needle and wherein each one of the first and second rods is configured to maintain the tip of a respective one of the first and second collapsible end portions in place within the tubular needle.

There is further provided, in accordance with an embodiment, a kit for repairing a tear in a meniscus tissue, the kit comprising: an implant comprising: a flexible tube, the flexible tube comprising: an end portion comprising a first elongated hardened element located at a tip of the end portion, and a collapsible end portion comprising a second elongated hardened element threaded thereon, and an actuating element secured to the collapsible end portion; and an applicator configured to deploy the flexible tube in the meniscus tissue by puncturing the meniscus tissue to form two apertures passing through the tear and threading the end portion and the collapsible end portion through the two apertures, respectively, wherein, when: the end portion and the collapsible end portion are threaded through the two apertures, respectively, and the actuating element is pulled proximally, the collapsible end portion collapses proximally and forms a bulge in vicinity to the second elongated hardened element, and wherein: a length dimension of the first elongated hardened element is larger than a respective one of the two apertures, the bulge and a length dimension of the second elongated hardened element are larger than a respective one of the two apertures, thereby anchoring the flexible tube against a peripheral distal wall of the meniscus tissue.

In some embodiments, each of the first and second elongated hardened elements has an involute shape.

In some embodiments, each of the first and second elongated hardened elements are made of polymer.

In some embodiments, the collapsible end portion comprises a hardened tip and the actuating element is secured to the hardened tip.

In some embodiments, the applicator comprises: a first tubular needle configured to puncture the meniscus tissue to form a respective one of the two apertures, the first tubular needle comprising: a first opening configured to allow insertion of the first elongated hardened element into the first tubular needle, and a first rod positioned there within and configured to maintain the first elongated hardened element in place within the first tubular needle; a second tubular needle configured to puncture the meniscus tissue to form a respective one of the two apertures, the second tubular needle comprising: a second opening configured to allow insertion of the second elongated hardened element and of the collapsible end portion into the second tubular needle, and a second rod positioned there within and configured to maintain the second elongated hardened element and the collapsible end portion in place within the second tubular needle.

There is further provided, in accordance with an embodiment, a kit for repairing a tear in a meniscus tissue, the kit comprising: an implant comprising: a flexible tube, the flexible tube comprising: a first end portion comprising a first elongated hardened element located at a tip of the first end portion, and a second end portion comprising a second elongated hardened element threaded thereon and a pulling anchor located along the second end portion, and an actuating element secured to the pulling anchor and extending along the second end portion; and an applicator configured to deploy the flexible tube in the meniscus tissue by puncturing the meniscus tissue to form two apertures passing through the tear and threading the first end portion and the second end portion through the two apertures, respectively, wherein, when: the first end portion and the second end portion are threaded through the two apertures, respectively, and the actuating element is pulled proximally, a collapsible segment of the second end portion, extending from the pulling anchor towards a middle portion of the flexible tube, collapses towards the second elongated hardened element and forms a bulge larger than the second aperture, and wherein: a length dimension of the first elongated hardened element is larger than a respective one of the two apertures, a length dimension of the second elongated hardened element is larger than a respective one of the two apertures, thereby anchoring the flexible tube to the meniscus tissue.

In some embodiments, each of the first and second elongated hardened elements has an involute shape.

In some embodiments, each of the first and second elongated hardened elements are made of polymer.

In some embodiments, the applicator comprises: a first tubular needle configured to puncture the meniscus tissue to form a respective one of the two apertures, the first tubular needle comprising: a first opening configured to allow insertion of the first elongated hardened element into the first tubular needle, and a first rod positioned there within and configured to maintain the first elongated hardened element in place within the first tubular needle; a second tubular needle configured to puncture the meniscus tissue to form a respective one of the two apertures, the second tubular needle comprising: a second opening configured to allow insertion of the second elongated hardened element and of the second end portion into the second tubular needle, and a second rod positioned there within and configured to maintain the second elongated hardened element and the second end portion in place within the second tubular needle.

There is further provided, in accordance with an embodiment, a method for repairing a tear in a meniscus tissue, the method comprising: puncturing the meniscus tissue in two locations in a proximal wall of the meniscus tissue to form two apertures passing through the tear and exiting the meniscus tissue through a peripheral distal wall of the meniscus tissue; threading two collapsible end portions of a flexible tube through the two apertures, respectively; pulling proximally a first and a second actuating element segments secured to the first and second collapsible end portions and extending along the first and second collapsible end portions, respectively, wherein the first and second collapsible end portions each collapses proximally and forms a bulge larger than a respective one of the two apertures, thereby anchoring the flexible tube against the peripheral distal wall of the meniscus tissue.

In some embodiments, each one of the first and second actuating element segments exits the flexible tube through a middle portion of the flexible tube.

In some embodiments, each one of the first and second actuating element segments extends along an inner void of a respective one of the first and second collapsible end portions and wherein each one of the first and second collapsible end portions collapses into its inner void.

In some embodiments, each one of the first and second actuating element segments is threaded laterally and repeatedly through a respective one of the first and second collapsible end portions, and wherein pulling proximally the first and second actuating element segments, folds each one of the first and second collapsible end portions laterally and repeatedly on itself In some embodiments, each one of the first and second collapsible end portions comprises a hardened portion located along a respective one of the first and second collapsible end portions at a predefined distance from a tip of the respective one of the first and second collapsible end portions, and wherein pulling proximally each of the first and second actuating element segments: collapses each of the first and second collapsible end portions into a section of an inner void of a respective one of the first and second collapsible end portions formed between the respective tip and the respective hardened portion, and collapses the hardened portion of each of the first and second collapsible end portions into a remainder of the respective inner void.

In some embodiments: each of the first and second collapsible end portions comprises a hardened tip, the first actuating element segment is secured to the hardened tip of the first collapsible end portion, and the second actuating element segment is secured to the hardened tip of the second collapsible end portion.

In some embodiments, the hardened tip of each of the first and second collapsible end portions comprises barbs, and wherein the barbs are configured to secure each hardened tip to a respective one of the first and second collapsible end portions when it is collapsed.

In some embodiments, the method further comprises a first actuating element comprising the first actuating element segment and a second actuating element comprising the second actuating element segment.

In some embodiments, puncturing the meniscus tissue is performed by two tubular needles of an applicator, the method further comprising placing a tip of each one of the first and second collapsible end portions in the two tubular needles, respectively, wherein the tip of each one of the first and second collapsible end portions is maintained in place by a rod located within each one of the two tubular needles, respectively, wherein threading of the two collapsible end portions further comprises retracting the rod located within each one of the two tubular needles to let the tip of each one of the first and second collapsible end portions out of a respective one of the two tubular needles through an opening in each respective one of the two tubular needles.

There is further provided, in accordance with an embodiment, a method for repairing a tear in a meniscus tissue, the method comprising: puncturing the meniscus tissue in two locations in a proximal wall of the meniscus tissue to form two apertures passing through the tear and exiting the meniscus tissue through a peripheral distal wall of the meniscus tissue; threading an end portion of a flexible tube and a first elongated hardened element located at a tip of the end portion through a respective one of the two apertures, wherein the first elongated hardened element is placed beyond the peripheral distal wall; threading a collapsible end portion of the flexible tube and a second elongated hardened element of the collapsible end portion threaded thereon, through a respective one of the two apertures, wherein the second elongated hardened element and a section of the collapsible end portion extending distally there from are placed beyond the peripheral distal wall; pulling proximally an actuating element segments secured to the collapsible end portion and extending along the collapsible end portion, wherein the section of the collapsible end portion collapses proximally and forms a bulge in vicinity to the second elongated hardened element, and wherein: a length dimension of the first elongated hardened element is larger than a respective one of the two apertures, the bulge and a length dimension of the second elongated hardened element are larger than a respective one of the two apertures, thereby anchoring the flexible tube against a peripheral distal wall of the meniscus tissue.

In some embodiments, each of the first and second elongated hardened elements has an involute shape.

In some embodiments, each of the first and second elongated hardened elements are made of polymer.

In some embodiments, the collapsible end portion comprises a hardened tip and the actuating element is secured to the hardened tip.

In some embodiments, puncturing of the meniscus tissue is performed by a first and a second tubular needles of an applicator, the method further comprising: placing the first elongated hardened element in the first tubular needle parallelly with respect to the first tubular needle, wherein the first elongated hardened element is maintained in place by a first rod located within the first tubular needle, and placing the second elongated hardened element and the collapsible end portion in the second tubular needle, wherein the second elongated hardened element is placed parallelly with respect to the second tubular needle, and wherein the second elongated hardened element and the collapsible end portion are maintained in place by a second rod located within the first tubular needle, wherein: threading the end portion and the first elongated hardened element comprises retracting the first rod to let the first elongated hardened element out of the first tubular needle through a first opening of the first tubular needle, and threading the collapsible end portion and the second elongated hardened element comprises retracting the second rod to let the second elongated hardened element and the collapsible end portion out of the second tubular needle through a second opening of the second tubular needle.

There is further provided, in accordance with an embodiment, a method for repairing a tear in a meniscus tissue, the method comprising: puncturing the meniscus tissue in two locations in a proximal wall of the meniscus tissue to form a first and a second apertures passing through the tear and exiting the meniscus tissue through a peripheral distal wall of the meniscus tissue; threading a first end portion of a flexible tube and a first elongated hardened element located at a tip of the first end portion through the first aperture, wherein the first elongated hardened element is placed beyond the peripheral distal wall; threading a second end portion of the flexible tube, back and forth through the second aperture, wherein a second elongated hardened element threaded on the second end portion and a pulling anchor located along the second end portion are placed at different sides with respect to the second aperture; and pulling proximally an actuating element secured to the pulling anchor and extending along the second end portion, wherein a collapsible segment of the second end portion, extending from the pulling anchor towards the middle portion of the flexible tube, collapses towards the second elongated hardened element and forms a bulge larger than the second aperture, and wherein: a length dimension of the first elongated hardened element is larger than the first aperture, and a length dimension of the second elongated hardened element is larger than the second aperture, thereby anchoring the flexible tube to the meniscus tissue.

In some embodiments, puncturing of the meniscus tissue is performed by a first and a second tubular needles of an applicator, the method further comprising: placing the first elongated hardened element in the first tubular needle parallelly with respect to the first tubular needle, wherein the first elongated hardened element is maintained in place by a first rod located within the first tubular needle, and placing the second elongated hardened element and the second end portion in the second tubular needle, wherein the second elongated hardened element is placed parallelly with respect to the second tubular needle, and wherein the second elongated hardened element and the second end portion are maintained in place by a second rod located within the second tubular needle, wherein: threading the end portion and the first elongated hardened element comprises retracting the first rod to let the first elongated hardened element out of the first tubular needle through a first opening of the first tubular needle, and threading the second end portion and the second elongated hardened element comprises retracting the second rod to let the second elongated hardened element and the second end portion out of the second tubular needle through a second opening of the second tubular needle.

There is further provided, in accordance with an embodiment, a method for joining at least two elements, the method comprising: forming a first aperture passing through the at least two elements; threading a first collapsible end portion of a flexible tube through the first aperture; pulling proximally a first actuating element segment secured to the first collapsible end portion and extending along the first collapsible end portion, wherein the first collapsible end portion collapses proximally and forms a bulge larger than the first aperture, thereby anchoring the flexible tube against a rim of the first aperture.

In some embodiments, the method further comprises: forming a second aperture passing through the at least two elements; threading a second collapsible end portion of the flexible tube through the second aperture; and pulling proximally a second actuating element segment secured to the second collapsible end portion and extending along the second collapsible end portion, wherein the second collapsible end portion collapses proximally and forms a bulge larger than the second aperture, thereby anchoring the flexible tube against a rim of the second aperture.

In some embodiments, each one of the first and second actuating element segments exits the flexible tube through a middle portion of the flexible tube.

In some embodiments, each one of the first and second actuating element segments extends along an inner void of a respective one of the first and second collapsible end portions and wherein each one of the first and second collapsible end portions collapses into its inner void.

In some embodiments, each one of the first and second actuating element segments is threaded laterally and repeatedly through a respective one of the first and second collapsible end portions, and wherein pulling proximally each one of the first and second actuating element segments, folds each one of the first and second collapsible end portions laterally and repeatedly on itself, respectively.

In some embodiments, each one of the first and second collapsible end portions comprises a hardened portion located along a respective one of the first and second collapsible end portions at a predefined distance from a tip of the respective one of the first and second collapsible end portions, and wherein pulling proximally each one of the first and second actuating element segments: collapses each one of the first and second collapsible end portions, respectively, into a section of an inner void of a respective one of the first and second collapsible end portions formed between the respective tip and the respective hardened portion, and collapses the hardened portion of each one of the first and second collapsible end portions into a remainder of the respective inner void.

In some embodiments: each one of the first and second collapsible end portions comprises a hardened tip, the first actuating element segment is secured to the hardened tip of the first collapsible end portion, and the second actuating element segment is secured to the hardened tip of the second collapsible end portion.

In some embodiments, the hardened tip of each one of the first and second collapsible end portions comprises barbs, and wherein the barbs are configured to secure the hardened tip of each one of the first and second collapsible end portions to a respective one of the first and second collapsible end portions when it is collapsed.

In some embodiments, the method further comprises a first actuating element comprising the first actuating element segment and a second actuating element comprising the second actuating element segment.

There is further provided, in accordance with an embodiment, a method for joining at least two elements, the method comprising: forming two apertures passing through the at least two elements; threading an end portion of a flexible tube and a first elongated hardened element located at a tip of the end portion through a respective one of the two apertures, wherein the first elongated hardened element is placed beyond a distal rim of the respective one of the two apertures; threading a collapsible end portion of the flexible tube and a second elongated hardened element threaded thereon through a respective one of the two apertures, wherein the second elongated hardened element and a section of the collapsible end portion extending distally there from are placed beyond a distal rim of the respective one of the two apertures; pulling proximally an actuating element secured to the collapsible end portion and extending along the collapsible end portion, wherein the section of the collapsible end portion collapses proximally and forms a bulge in vicinity to the second elongated hardened element, and wherein: a length dimension of the first elongated hardened element is larger than a respective one of the two apertures, the bulge and a length dimension of the second elongated hardened element are larger than a respective one of the two apertures, thereby anchoring the flexible tube against the distal rim of each one of the two apertures.

In some embodiments, each of the first and second elongated hardened elements has an involute shape.

In some embodiments, each of the first and second elongated hardened elements are made of polymer.

In some embodiments, the collapsible end portion comprises a hardened tip and the actuating element is secured to the hardened tip.

There is further provided, in accordance with an embodiment, a method for joining at least two elements, the method comprising: forming a first and a second aperture passing through the at least two elements; threading a first end portion of a flexible tube and a first elongated hardened element located at a tip of the first end portion through the first aperture, wherein the first elongated hardened element is placed beyond a distal rim of the respective one of the two apertures; threading a second end portion of the flexible tube, back and forth through the second aperture, wherein a second elongated hardened element threaded on the second end portion and a pulling anchor located along the second end portion are placed at different sides with respect to the second aperture; and pulling proximally an actuating element secured to the pulling anchor and extending along the second end portion, wherein a collapsible segment of the second end portion, extending from the pulling anchor towards a middle portion of the flexible tube, collapses towards the second elongated hardened element and forms a bulge larger than the second aperture, and wherein: a length dimension of the first elongated hardened element is larger than the first aperture, and a length dimension of the second elongated hardened element is larger than the second aperture, thereby anchoring the flexible tube to the two elements.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 3A-3D show perspective views of a collapsible end portion of a mesh flexible tube of the device of FIG. 1 in different states while an actuating element segment coupled with the collapsible end portion is pulled;

FIGS. 4A-4D show semi-transparent vertical sections of the collapsible end portion of FIGS. 3A-3D, respectively;

FIGS. 14A-14E show top views of an applicator deploying an implant in a meniscus tissue according to the method of FIG. 12;

FIG. 17A shows a cross-section of an elongated hardened element including a bore and made of solid polymer;

FIG. 17B shows a cross-section of an exemplary device including two elongated hardened elements such as the elongated hardened element of FIG. 17A and arranged in a U-shape;

FIG. 17C shows a collapsible end portion of a flexible mesh tube of the device of FIG. 17B, when collapsed;

FIG. 18A shows a top transparent view of an exemplary kit including an applicator and an implant;

FIG. 18B shows a top transparent view of another exemplary kit including an applicator and an implant;

FIGS. 23A-23E show side and perspective views of an implant deployed in a meniscus tissue according to the method of FIG. 22.

DETAILED DESCRIPTION

Figure 1:
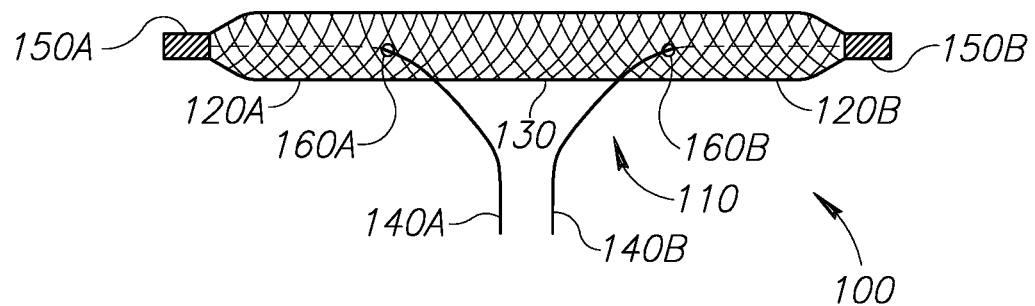
FIG. 1 shows a side view of an exemplary device including a mesh flexible tube and two actuating elements.

The disclosed devices, kits and methods may be used for anchoring in various industrial and medical fields. Generally, the disclosed device may include an elongated tube, whether hollow or solid, and an actuating element secured to an end of the elongated tube; an end portion of the tube may be inserted into an aperture, and the actuating element may then be pulled. During this pulling, a portion of the elongated tube may collapse (such as form multiple folds one over the other) and form a bulge which serves as an anchor at an opposite side of the aperture.

This anchor may be used for firmly securing the tube to an element in which the aperture is situated. Optionally, in order to release the anchor, the actuating element may be pushed, thereby expanding the collapsed portion of the tube and eliminating the bulge.

In a more complex variety of the device, two or more such bulges may be formed at different areas of the tube, such as at its two opposing ends or even along its length. This may allow the convenient anchoring of two or more elements to one another.

In the medical field, the present device may be used in surgical procedures where fixation of two or more tissues to one another is required. Examples include fixation of bones, soft tissues, or any combination thereof. Additionally, one or more surgical implants may be affixed to a bodily tissue using the device.

For simplicity of discussion, the present devices, kits and methods are discussed herein with reference to meniscus repair, in which a tear in the meniscus tissue is repaired by affixing together the two opposing sides of the tear. However, those of skill in the art will recognize that the devices, kits and methods may be similarly used for many other medical and/or industrial applications.

The use of the disclosed devices, kits and methods in meniscus repair procedures may be relatively easy and fast and may provide a firm and reliable closure of the tear and minimization of the damage.

The term "two elements", as referred to herein with respect to joining of these elements, may relate to two separate elements or to two portions of the same element (i.e., each portion is referred to as an element). For example, two separate elements may be joined together, or two portions of an element may be joined together, for example, to close a tear in the element which divides the element into two portions.

The term "collapse" and its derivations, as referred to herein with respect to some component of the disclosed devices and kits, including a portion of the flexible tube of the disclosed devices and kits, may relate to the folding of the component on or into itself The term "pulling proximally" and its derivations as referred to herein with respect to an actuating element, an actuating element segment or a flexible tube of the disclosed devices and kits, may include each direction which causes a portion of a flexible tube of the disclosed devices and kits to collapse.

Disclosed herein is a device, which may include a flexible tube and an actuating element segment. The flexible tube may include a collapsible end portion. The actuating element segment may extend along the collapsible end portion. The actuating element segment may be secured to the collapsible end portion.

The collapsible end portion may be threaded through an aperture. When the first actuating element segment is pulled proximally, the collapsible end portion may collapse proximally and form a bulge larger than the first aperture. Thus, the flexible tube may be anchored against a rim of the aperture.

The flexible tube may be made of flexible materials such as rubber and/or a woven material (i.e., a mesh), e.g., woven threads. The collapsible end portion may be made of materials which collapse when applying force on them, e.g., in a specific direction. Thus, the collapsible end portion may be, for example, a mesh collapsible end portion, i.e., made of a woven material or a knitted material. The actuating element segment may be, for example, a thread or a rigid roll.

Figure 2:
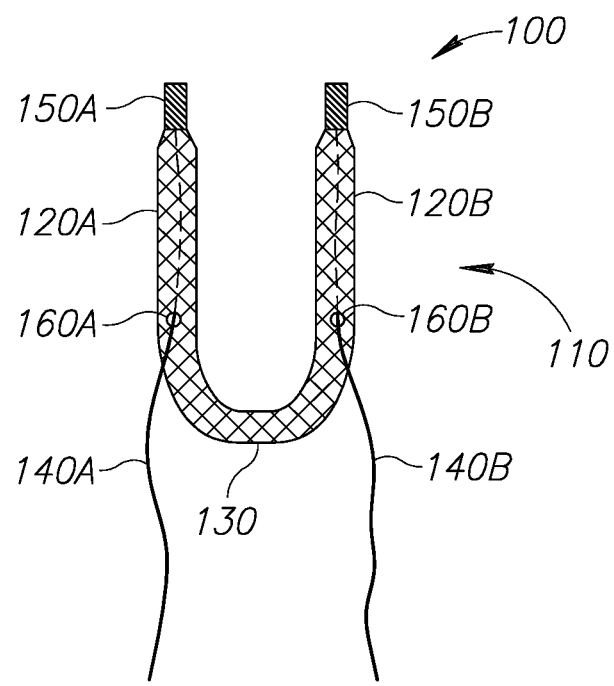
FIG. 2 shows a vertical section of the device of Fig.1 when it is arranged in a U-shape.

In some embodiments, the flexible tube may include two collapsible end portions and two actuating element segments, correspondingly. Reference is now made to FIGS. 1-4D. FIG. 1 shows a side view of an exemplary device 100 including a mesh flexible tube 110 and two actuating elements 140A and 140B. FIG. 2 shows a vertical section of device 100 of Fig.1 when it is arranged in a U-shape. FIGS. 3A-3D show perspective views of a collapsible end portion 120A of mesh flexible tube 110 of device 100 of FIG. 1 in different states while an actuating element segment coupled with collapsible end portion 120A is pulled. FIGS. 4A-4D show vertical sections of the collapsible end portion of FIGS. 3A-3D, respectively.

Exemplary device 100 may include a flexible mesh tube 110 and two actuating element segments 140A and 140B. Flexible mesh tube 110 may include two collapsible end portions 120A and 120B and a middle portion 130. Each of collapsible end portions 120A and 120B may optionally include a hardened tip 150A and 150B, respectively. Actuating element segments 140A and 140B may be secured to hardened tips 150A and 150B of collapsible end portions 120A and 120B, respectively. However, in this and every other embodiment of the specification, the term "hardened tip" may also relate to a configuration in which an actuating element segment is secured to a collapsible end portion by other means, such as glue, knotting and/or the like.

Each of actuating element segments 140A and 140B may extend along collapsible end portions 120A and 120B, respectively. Actuating element segments 140A and 140B may extend along an inner void of collapsible end portions 120A and 120B, respectively, as shown in FIG. 2. An end portion of each of actuating element segments 140A and 140B may be located externally to flexible mesh tube 110, thus facilitating pulling of actuating element segments 140A and 140B. The end portion of each of actuating element segments 140A and 140B may exit flexible mesh tube 110 through an opening 160A and 160B in flexible mesh tube 110, respectively. Actuating element segments 140A and 140B may be segments of a single actuating element. Alternatively, device 110 may include two separate actuating elements, while one of the actuating elements includes actuating element segment 140A and the other includes actuating element segment 140B.

Collapsible end portions 120A and 120B may be threaded through a first and a second aperture, respectively, while leaving middle portion 130 out of the first and second apertures. Thus, device 100 may be formed in a U-shape, as exemplified in FIG. 2, in order to facilitate such threading. The end portions of actuating element segments 140A and 140B may be then positioned proximally (i.e., with respect to an operator of device 100), facilitating proximal pulling of each of element segments 140A and 140B. Following the pulling of each of collapsible end portions 120A and 120B, they may collapse proximally and respectively and form a bulge larger than a respective one of the first and second apertures. Each of collapsible end portions 120A and 120B may collapse into its inner void.

Hardened tips 150A and 150B may be formed, for example, by melting the material of flexible mesh tube 110 and/or by over-molding a certain material or glue on the flexible mesh tube. In some medical applications, due to biocompatibility concerns, it may be desired to use the melting technique.

Hardened tips 150A and 150B may be of different shapes and other than rectangular, as shown in FIGS. 1 and 2.

FIGS. 3A-3D and 4A-4D exemplify the collapsing of collapsible end portion 120A when actuating element segment 140A is pulled proximally. In FIG. 3A and 4A actuating element segment 140A is pulled proximally while the direction of pulling is indicated in FIGS. 3A by an arrow and the letter "F", which stands for "Force". In FIGS. 3B and 4B, hardened tip 150A is pulled proximally by actuating element segment 140A and collapsible end portion 120A begins to collapse into its inner void and a bulge is starting to form. In FIGS. 3C and 4C, collapsible end portion 120A continues to collapse while actuating element segment 140A is still pulled proximally. In FIGS. 3D and 4D, the pulling is stopped, and a final bulge is formed. By forming each bulge, larger than a respective one of the first and second apertures, flexible mesh tube 110 may be anchored against a rim of each one of the first and second apertures.

Figure 5A:
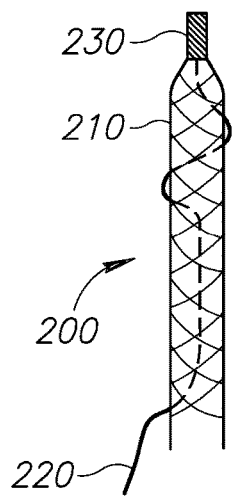
FIG. 5A shows a perspective view of a collapsible end portion of an exemplary mesh flexible coupled with a laterally and repeatedly threaded actuating element segment.
Figure 5B:
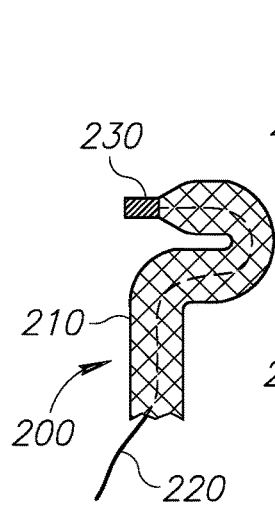
FIG. 5B shows a perspective view of the collapsible end portion of FIG. 5A when the actuating element segment is pulled.

In some embodiments an actuating element segment may be threaded laterally and repeatedly through a collapsible end portion. In such embodiments, when the actuating element segment is pulled, the collapsible end portion may fold laterally and repeatedly on itself. Reference is now made to FIGS. 5A-5D. FIG. 5A shows a perspective view of a collapsible end portion 210 of an exemplary mesh flexible tube 200 coupled a laterally and repeatedly threaded actuating element segment 220. FIG. 5B shows a perspective view of the collapsible end portion 210 of FIG. 5A when actuating element segment 220 is pulled. Collapsible end portion 210 may optionally include a hardened tip 230. Actuating element segment 220 may be threaded laterally and repeatedly, for example, twice, as shown in FIG. 5A. Thus, when pulled proximally, collapsible end portion 210 may fold on itself, as shown in FIG. 5B.

Figure 5C:
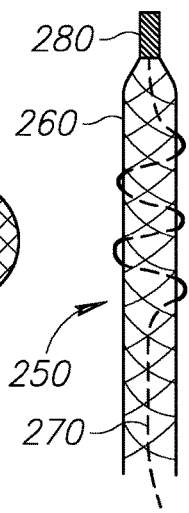
FIG. 5C shows a perspective view of a collapsible end portion of another exemplary mesh flexible coupled with a laterally and repeatedly threaded actuating element segment.
Figure 5D:
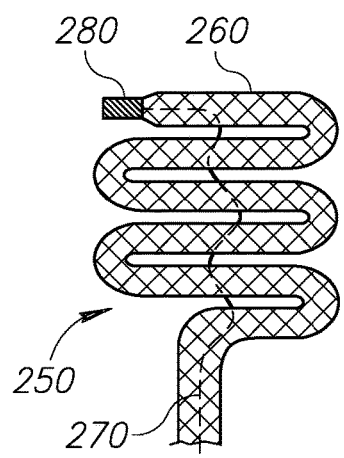
FIG. 5D shows a perspective view of the collapsible end portion of FIG. 5C when the actuating element segment is pulled.

FIG. 5C shows a perspective view of a collapsible end portion of another exemplary mesh flexible tube 250 coupled with a laterally and repeatedly threaded actuating element segment 270. Mesh flexible tube 250 may be hollow or even solid; in the latter case, segment 270 is threaded through the solid body of tube 250. FIG. 5D shows a perspective view of the collapsible end portion of FIG. 5C when actuating element segment 270 is pulled. Collapsible end portion 260 may optionally include a hardened tip 280. Actuating element segment 270 may be threaded laterally and repeatedly through collapsible end portion 260, for several times, as shown in FIG. 5C. Thus, when pulled proximally, collapsible end portion 260 may fold on itself several times, as shown in FIG. 5D.

Figure 6A:
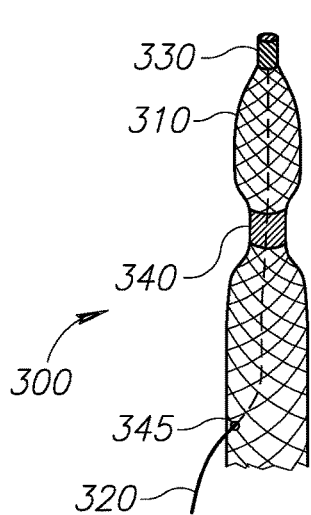
FIG. 6A shows a semi-transparent view of a collapsible end portion of a mesh flexible tube including a hardened coupled with an actuating element segment and a hardened portion located along the collapsible end portion.
Figure 6B:
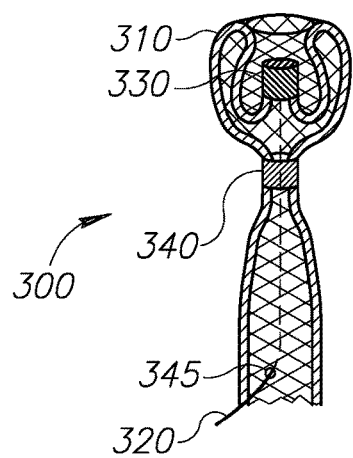
FIGS. 6B-6C show semi-transparent vertical sections of the collapsible end portion of FIG. 6A in different states while the actuating element segment is pulled.
Figure 6C:
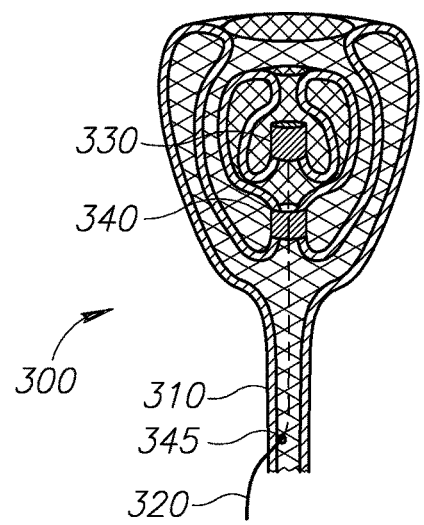

Reference is now made to FIGS. 6A-6C. FIG. 6A shows a perspective transparent view of a collapsible end portion 310 of a mesh flexible tube 300, optionally including a hardened tip 330 coupled with an actuating element segment 320 and a hardened portion 340 located along the collapsible end portion. In further embodiments (not shown), further hardened portions such as portion 340 may be located along a mesh flexible tube, to provide means for further folding of the tube. FIGS. 6B-6C show perspective transparent views of vertical sections of collapsible end portion 310 of FIG. 6A in different states while actuating element segment 320 is pulled. The hardened portion may be formed, for example, by hardening a portion of the flexible tube that circumscribe or partially circumscribe the flexible tube.

Collapsible end portion 310 may include hardened portion 340 located along collapsible end portion 310 at a predefined distance from a tip of collapsible end portion 310. Collapsible end portion 310 may further include hardened tip 330 located at the tip of collapsible end portion 310. Hardened portion 340 may be tubular in order to allow free passage of actuating element segment 320 through collapsible end portion 310.

When actuating element segment 320 is pulled proximally, collapsible end portion 310 may collapse into a section of an inner void of collapsible end portion 310 formed between hardened tip 330 and hardened portion 340, as shown in FIG. 6B. As the pulling of actuating element segment 320 continues, hardened portion 340 collapses into the remainder of the inner void of collapsible end portion 310, as shown in FIG. 6C.

Figure 7A:
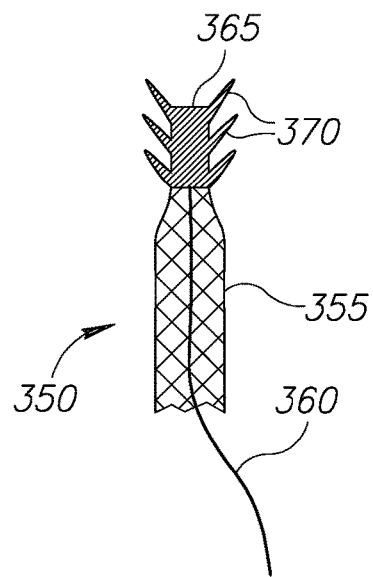
FIG. 7A shows a semi-transparent vertical section of a collapsible end portion of a mesh flexible tube coupled with an actuating element segment and including a hardened tip with barbs located at two opposite sides of the hardened tip.
Figure 7B:
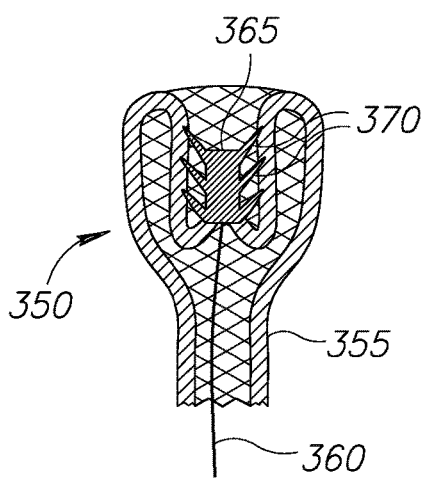
FIGS. 7B-7C show semi-transparent vertical sections of vertical sections of the collapsible end portion of FIG. 7A in different states while the actuating element segment is pulled.
Figure 7C:
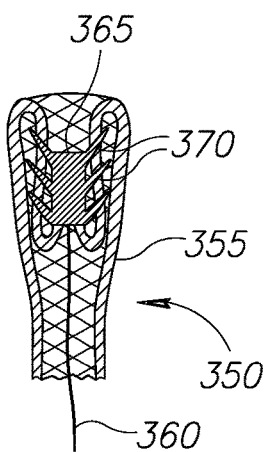
Figure 7D:
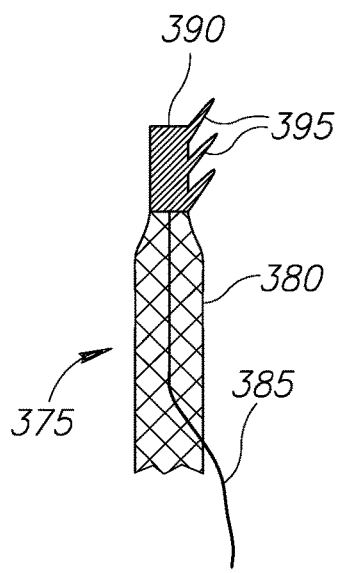
FIG. 7D shows a semi-transparent view of a collapsible end portion of a mesh flexible tube coupled with an actuating element segment and including a hardened tip with barbs located at one side of the hardened tip.
Figure 7E:
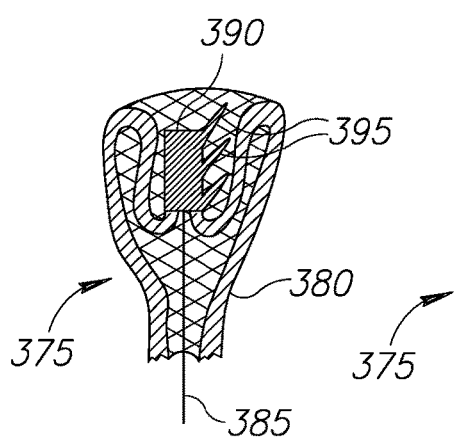
FIGS. 7E-7F show semi-transparent vertical sections of vertical sections of the collapsible end portion of FIG. 7D in different states while the actuating element segment is pulled.
Figure 7F:
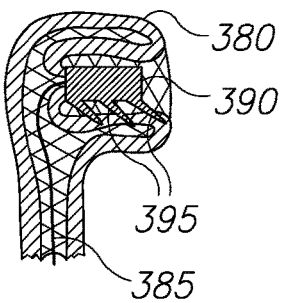

Reference is now made to FIGS. 7A-7F. FIG. 7A shows a perspective transparent view of a collapsible end portion 355 of a mesh flexible tube 350 coupled with an actuating element segment 360 and including a hardened tip with barbs located at two opposite sides of the hardened tip. FIGS. 7B-7C show perspective transparent views of vertical sections of the collapsible end portion 355 of FIG. 7A in different states while actuating element segment 360 is pulled. FIG. 7D shows a perspective transparent view of a collapsible end portion 380 of a mesh flexible tube 375 coupled with an actuating element 385 and including a hardened tip with barbs located at one side of the hardened tip. FIGS. 7E-7F show perspective transparent views of vertical sections of collapsible end portion 380 of FIG. 7D in different states while actuating element segment 385 is pulled.

Collapsible end portion 355 may include a hardened tip 365. Hardened tip 365 may include barbs 370 located at two opposite sides of hardened tip 365. When actuating element segment 360 is pulled proximally and collapsible end portion 355 collapses, barbs 370 may secure hardened tip 365 to collapsible end portion 355 by grasping collapsible end portion 355 at two respective opposite locations. Collapsible end portion 380 may include a hardened tip 390. Hardened tip 390 may include barbs 395 located at a side of hardened tip 390. When actuating element segment 385 is pulled proximally and collapsible end portion 380 collapses, barbs 395 may secure hardened tip 390 to collapsible end portion 380 by grasping collapsible end portion 380 at a respective location. In some embodiments, hardened tips 365 and 390 may include barbs such as barbs 370 and 395 in various numbers and located thereon according to various configurations.

In some embodiments, the disclosed devices may be used for repairing a tear in a meniscus tissue. In some embodiments, such devices may include two collapsible end portions and two actuating element segments, correspondingly. The two collapsible end portions may be threaded through two apertures made in the meniscus tissue through the tear in order to bring two edges of the tear closer together. When the two actuating element segments are pulled proximally, the flexible tube may be anchored against a peripheral distal wall of the meniscus tissue thereby maintaining the tear closed, either fully (i.e. opposing surfaces of the tear are in contact) or almost fully (i.e. opposing surfaces of the tear are at a very short distance from each other, such as 1-2 tenths of a millimeter apart; the surfaces may contact each other at some points).

A kit for repairing a tear in a meniscus tissue is herein disclosed. The kit may include an implant and an applicator. The implant may be similar to the devices disclosed herein.

The applicator may be configured to deploy the implant in the meniscus tissue. The applicator may be used to puncture the meniscus tissue in order to form at least one aperture passing through the tear. At least one collapsible end portion of a flexible tube of the implant may be then threaded through the aperture in order to bring the edges of the tear closer together. Pulling the actuating element segment which is secured to the collapsible end portion may anchor the implant to the meniscus tissue thus maintaining the tear closed.

Figures 8A, 8B, 8C:
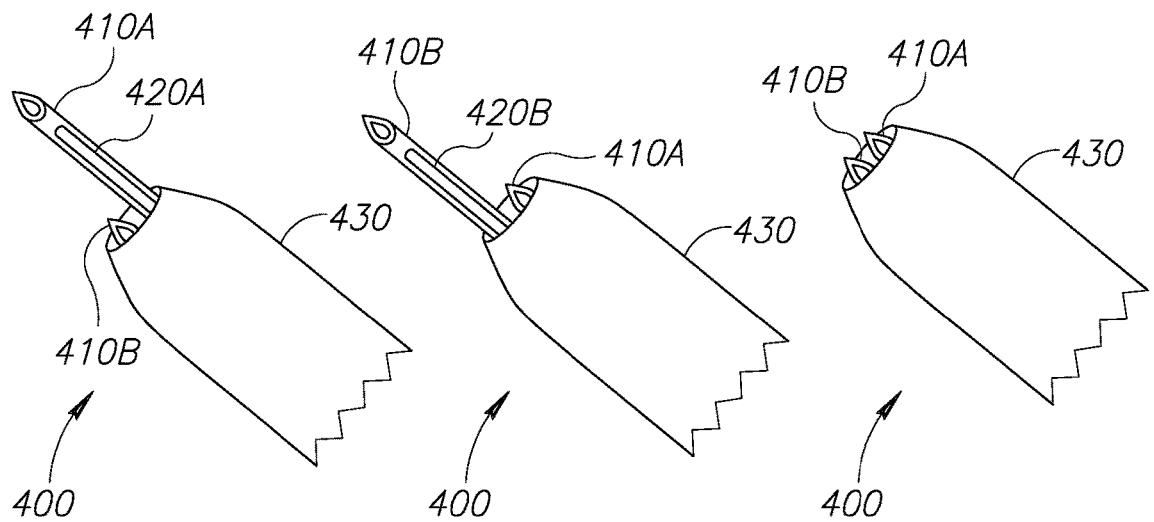
FIG. 8A shows a perspective top view of an exemplary applicator of a kit which includes two tubular needles when one of the tubular needles is in an operative mode.
FIG. 8B shows a perspective top view of the exemplary applicator of FIG. 8A when the other tubular needle is in an operative mode.
FIG. 8C shows a perspective top view of the exemplary applicator of FIG. 8A when in a non-operative mode.
Figures 9A, 9B, 9C:
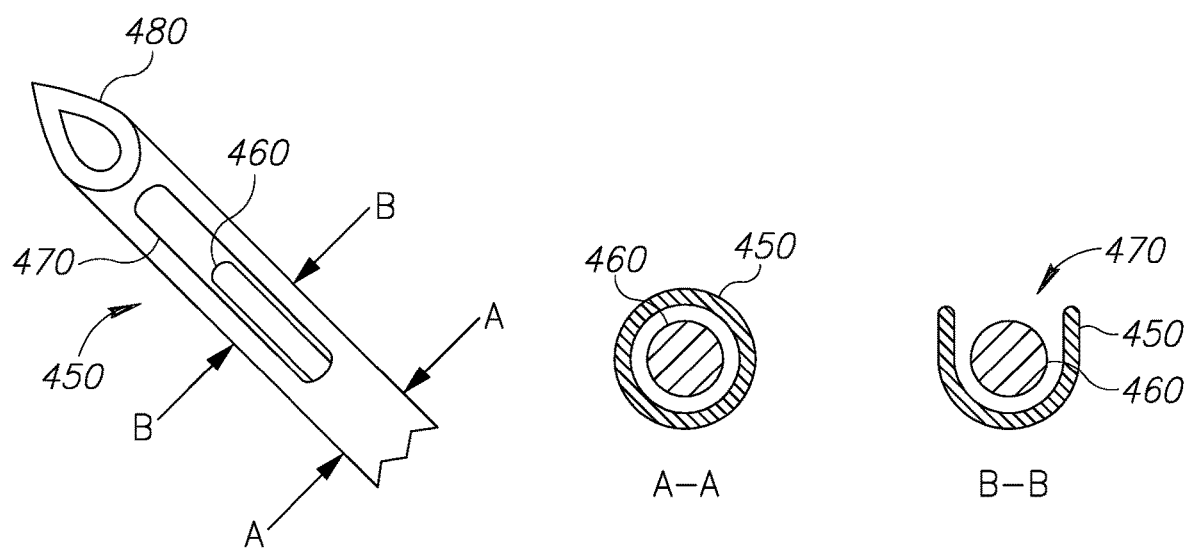
FIG. 9A shows an isometric top view of a tubular needle of an exemplary applicator.
FIG. 9B shows a cross-section along line A-A of the tubular needle of FIG. 9A.
FIG. 9C shows a cross section along line B-B of the tubular needle of FIG. 9A.
Figure 10:
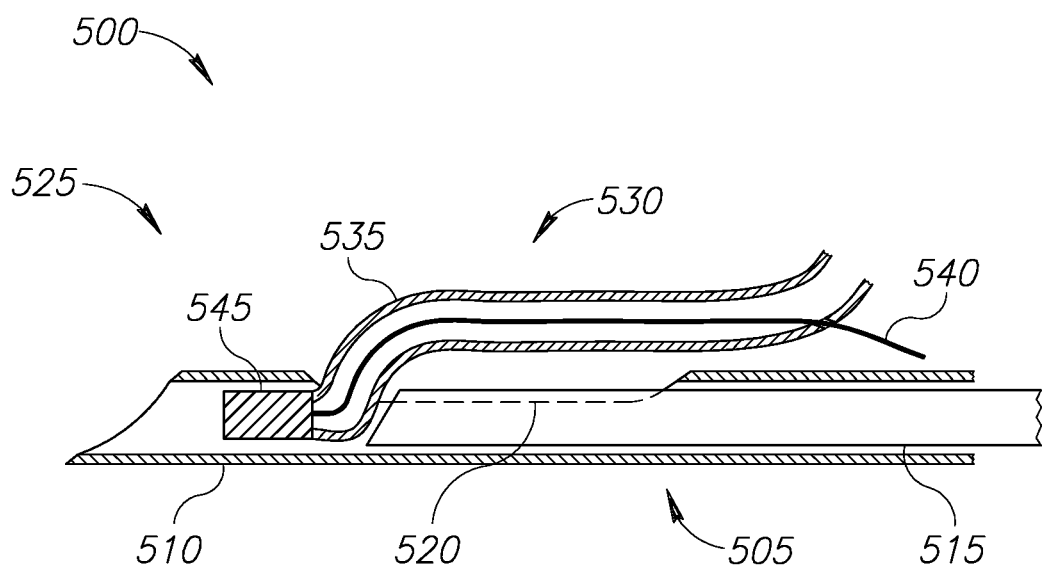
FIG. 10 shows a side view, partially cross-sectional, of a vertical section of an exemplary kit including an applicator and an implant.

Reference is now made to FIGS. 8A-10. FIG. 8A shows a perspective top view of an exemplary applicator 400 of a kit which includes two tubular needles when one of the tubular needles is in an operative mode. The term "tubular needle", along the specification, may relate to a needle having a circular cross section or any other shape of cross section. FIG. 8B shows a perspective top view of exemplary applicator 400 of FIG. 8A when the other tubular needle is in an operative mode. FIG. 8C shows a perspective top view of exemplary applicator 400 of FIG. 8A when in a non-operative mode. FIG. 9A shows an isometric top view of a tubular needle 450 of an exemplary applicator. FIG. 9B shows a cross section along line A-A of tubular needle 450 of FIG. 9A. FIG. 9C shows a cross-section along line B-B of tubular needle 450 of FIG. 9A. FIG. 10 shows a side view of a vertical section of an exemplary kit 500 including an applicator 505 and an implant 525.

Applicator 400 may include two tubular needles 410A and 410B. Applicator 400 may further include a housing 430 configured to hold needles 410A and 410B and cover them when applicator 400 is in a non-operative mode as show in FIG. 8C. Each of tubular needles 410A and 410B may include an opening 410A and 410B, respectively and a rod (not shown).

With reference to FIGS. 9A-9C, tubular needle 450, which is similar to tubular needles 410A and 410B, may include a rod 460 and an opening 470. Tubular needle 450 may further include a front opening 480. Tubular needle 450 may be configured to puncture the meniscus tissue in order to form an aperture through the meniscus tissue. Opening 470 may be configured to allow insertion of a tip of a collapsible end portion of a flexible tube of the disclosed implant into tubular needle 450. Rod 460 may be positioned within tubular needle 450, i.e., in an inner void of tubular needle 450. Rod 460 may be configured to maintain the tip of the collapsible end portion in place within tubular needle 450. Opening 470 may be sufficiently long for enabling the disclosed implant to exit the void of tubular needle 450.

Referring now to FIG. 10, applicator 505 may include a tubular needle 510, a rod 515 and an opening 520. Implant 525 may include a flexible tube 530 and an actuating element segment 540. Flexible tube 530 may include a collapsible end portion 535. Collapsible end portion 535 may optionally include a hardened tip 545. Hardened tip 545 may be inserted into tubular needle 510 through opening 520. Rod 515 may be then pushed distally in order to hold collapsible end portion 535 against a distal rim of opening 520, thereby maintaining hardened tip 545 in place, i.e., within a distal portion of tubular needle 450.

Referring back to FIGS. 8A-8C, applicator 400 is shown in FIGS. 8A and 8B in operative modes. In FIG. 8A, tubular needle 410A is projected from housing 430 in order to puncture the meniscus tissue and deploy a respective collapsible end portion of the disclosed implant in the meniscus tissue. Tubular needle 410B is in a non-operative mode and therefore retracted. In FIG. 8B, tubular needle 410B is projected from housing 430 in order to puncture the meniscus tissue and deploy a respective collapsible end portion of the disclosed implant in the meniscus tissue. Tubular needle 410A is in a non-operative mode and therefore retracted. In FIG. 8C, applicator 400 is in a non-operative mode, i.e., both tubular needles 410A and 410B are retracted into housing 430.

In some embodiments, a collapsible end portion of the disclosed implant may be deployed in the meniscus tissue through another opening, such as top opening 480 of tubular needle 450 of FIGS. 9A-9C. In such embodiments, rode 460, for example, may be used to push the implant out of tubular needle 450 through top opening 480 in order to deploy it in the meniscus tissue.

Figure 11:
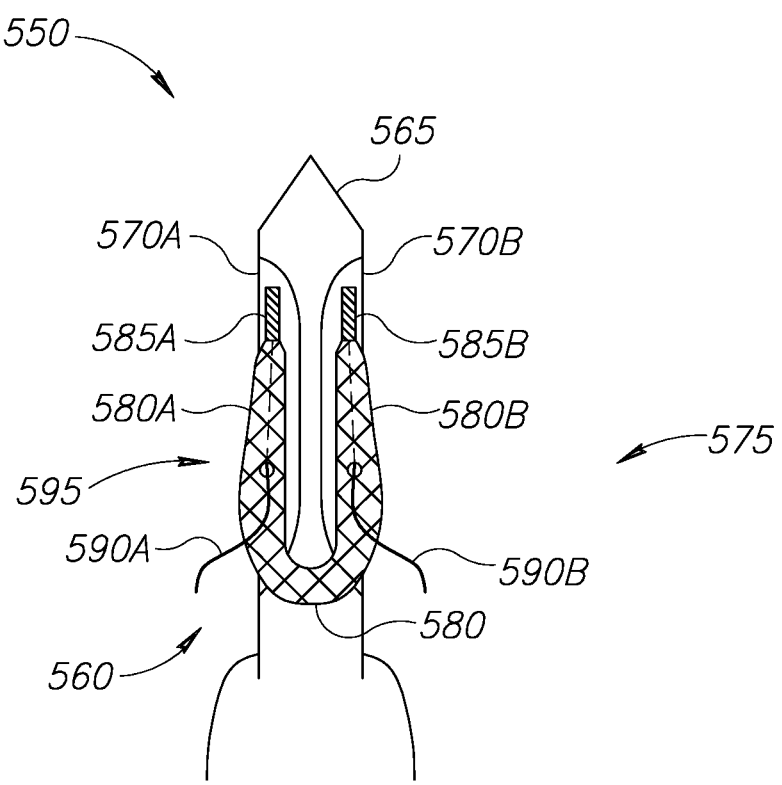
FIG. 11 shows a top view of an exemplary kit including an applicator and an implant, where the applicator includes a tubular needle, and when the mesh implant is positioned in the applicator.

In some embodiments, an applicator which includes only one tubular needle may be used to deploy the disclosed implant, while including a flexible tube with two collapsible end portions. Reference is now made to FIG. 11, which shows a top view of an exemplary kit 550 including an applicator 560 and an implant 575, where applicator 560 includes a tubular needle, and when implant 575 is positioned in applicator 560. Flexible mesh tube 595 may include two collapsible end portions 580A and 580B and a middle portion 580. Each of the two collapsible end portions 580A and 580B may include a hardened tip 585A and 585B, respectively. Applicator 560 may include a tubular needle 565, two openings 570A and 570B and two corresponding rods. The rods may be positioned within openings 570A and 570B and beneath flexible mesh tube 595 and hence not shown. Implant 575 may include a flexible mesh tube 595 and two actuating elements 590A and 590B. Tubular needle 565 may be configured to puncture the meniscus tissue to form two apertures in the meniscus tissue and deploy implant 575 through the two apertures in the meniscus tissue. Each of openings 570A and 570B may be configured to allow insertion of hardened tips 585A and 585B into tubular needle 565, respectively. Optionally, openings 570A and 570B may be partitioned.

Implant 575 may be positioned in applicator 560, as shown in Fig.11 (i.e., in a U-shape) in order to insert hardened tips 585A and 585B into openings 570A and 570B, respectively. The two rods may be then pushed distally within openings 570A and 570B, respectively, in order to maintain hardened tips 585A and 585B in place.

Figure 12:
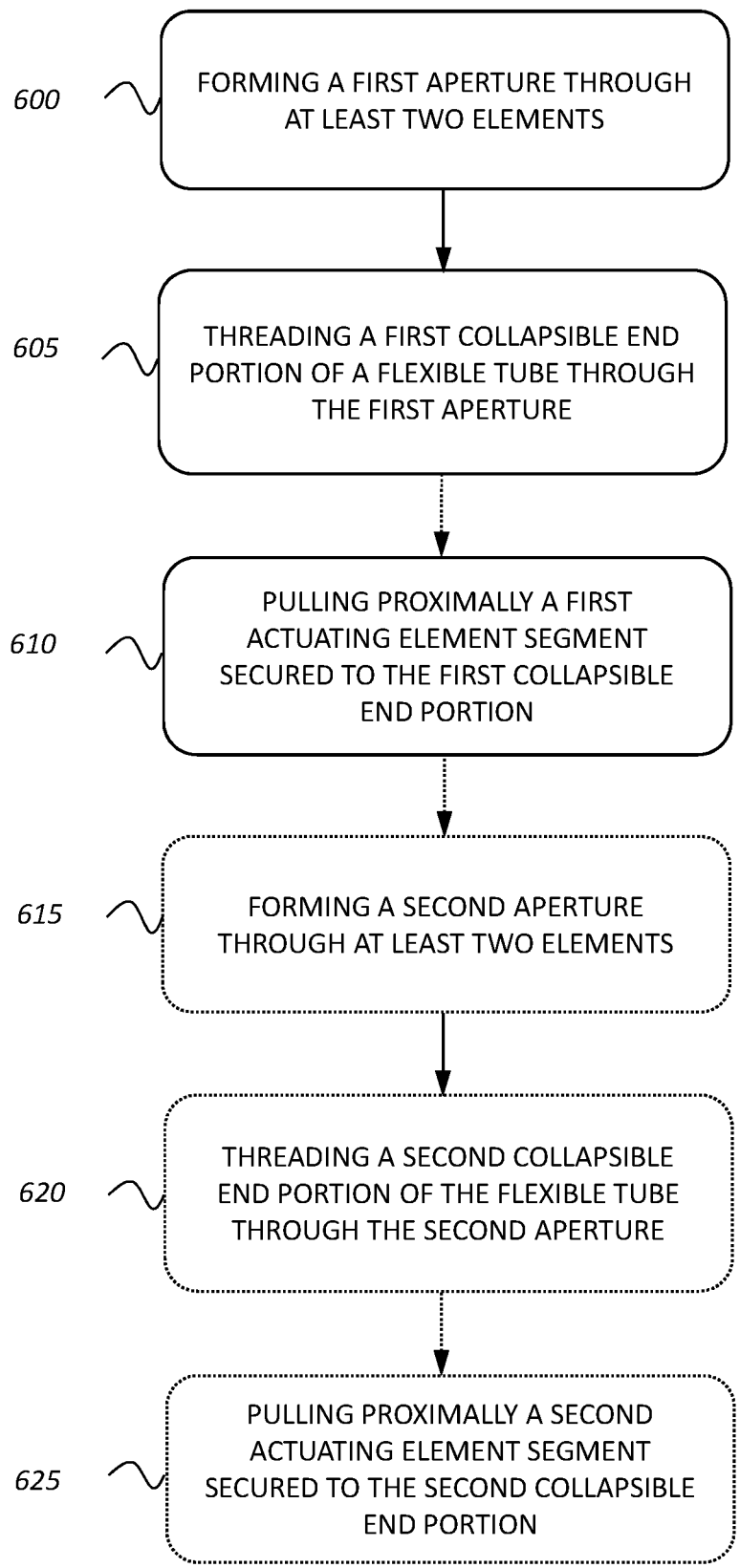
FIG. 12 shows a flowchart of a method for joining at least two elements, constructed and operative in accordance with an embodiment of the disclosed technique.

Reference is now made to FIG. 12 which shows a flowchart of a method for joining at least two elements, constructed and operative in accordance with an embodiment of the disclosed technique. In a step 600, a first aperture passing through the at least two elements is formed. The first aperture may be formed in the two or more elements by entering through the most proximal element of the two or more elements, passing through all of the other elements to be joined and exiting through the most distal element.

In a step 605, a first collapsible end portion of a flexible tube may be threaded through the first aperture, entering through the most proximal element and exiting through the most distal element. The flexible tube may be the flexible tube of the disclosed devices.

In a step 610, a first actuating element segment secured to the first collapsible end portion may be pulled proximally. The first actuating element segment may extend along the first collapsible end portion. The first collapsible end portion may then collapse proximally and form a bulge larger than the first aperture, thereby anchoring the flexible tube against a rim of the first aperture.

Optionally, the first actuating element segment may extend along an inner void of the first collapsible end portion and may exit the flexible tube through a middle portion of the flexible tube, as shown in FIGS. 3A-3D with respect to flexible mesh tube 110. The pulling of the first actuating element segment proximally may then collapse the collapsible end portion into its inner void.

Optionally, the first actuating element segment may be threaded laterally and repeatedly through a the first collapsible end portion, as shown in FIGS. 5A and 5C with respect to flexible mesh tubes 200 and 250. The pulling of the first actuating element segment proximally may then fold the first collapsible end portion laterally and repeatedly on itself, as shown in FIGS. 5B and 5D.

Optionally, the first collapsible end portion may include a hardened portion located along the first collapsible end portion at a predefined distance from a tip of the first collapsible end portion, as shown in FIG. 6A with respect to flexible mesh tube 300. Pulling of the first actuating element segment proximally may then collapse the first collapsible end portion into a section of an inner void of the first collapsible end portion formed between its tip and its hardened portion, as shown in FIG. 6B. Further pulling of the actuating element segment proximally may, in addition, collapse the hardened portion of the first collapsible end portion into the remainder of its inner void, as shown in FIG. 6C.

Optionally, the first collapsible end portion may include a hardened tip. The first actuating element segment may be secured to the hardened tip, advantageously to a center of a bottom surface of the hardened tip, as shown in FIGS. 3A 3D.

In an optional step 615, a second aperture passing through the at least two elements may be formed. This step may be similar to step 600.

In case the at least two elements are separable, they may be arranged to assure firm and effective joining of the two or more elements. The location of the entrance of the first and/or second aperture in the most proximal element and/or the path of the first and/or second aperture through the two or more elements may be selected to assure firm and effective joining of the two or more elements.

In an optional step 620, the second collapsible end portion of the flexible tube may be threaded through the second aperture. This step may be similar to step 605.

In a further optional step, the second collapsible end portion may be stretched distally, thereby bringing the bulge formed over the distal rim of the first aperture closer to the distal rim and a middle portion of the flexible tube closer to the proximal element (i.e., a proximal surface of the most proximal element).

In an optional step 625, a second actuating element segment secured to the second collapsible end portion may be pulled proximally. This step may be similar to step 620. The first actuating element segment and the second actuating element segment may be pulled in a separate manner.

Figure 13A:
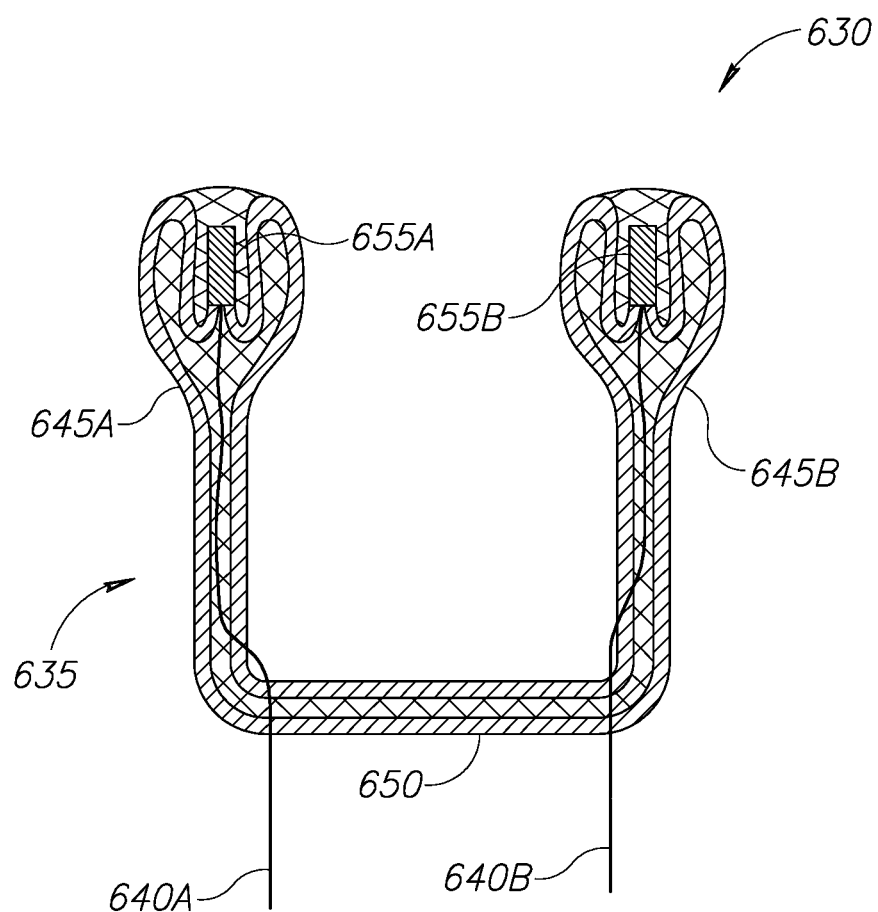
FIG. 13A shows a semi-transparent vertical section of a device including two separate actuating elements, when deployed and after pulling of the actuating elements.
Figure 13B:
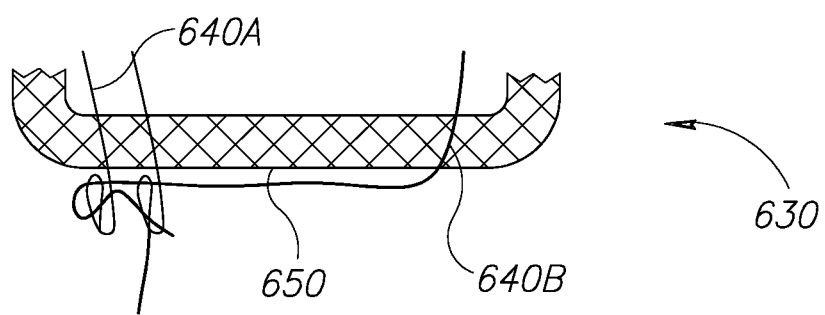
FIG. 13B shows a side view of a middle portion of the device of FIG. 13A, where the actuating elements are tied.

In an optional step, when the device includes two flexible separate actuating elements, such as threads, the two separate actuating elements may be tied. Reference is now made to FIGS. 13A and 13B. FIG. 13A shows a side view of a vertical section of a device including two separate and flexible actuating elements, when deployed and after pulling of the actuating elements. FIG. 13B shows a side view of a middle portion of the device of FIG. 13A, where the remainder of the actuating elements is tied. Tying of the remainder of the actuating elements may further anchor the flexible tube to the at least two elements and thereby the joining of these elements and/or may shorten the remainder of the actuating elements (i.e., so it may not be left hanging).

In some embodiments, the disclosed methods may be used for repairing a tear in a meniscus tissue. The method may then use the disclosed devices and kits for repairing a tear in a meniscus tissue. In such a case, the at least two elements to be joined are a peripheral distal wall of the meniscus tissue (also known as the peripheral portion of the meniscus) and a proximal wall of the meniscus tissue (also known as the free end portion of the meniscus). The two collapsible end portions may be threaded through two apertures made in the meniscus tissue through the tear in order to bring two edges of the tear closer together. When the two actuating element segments are pulled proximally, the flexible tube may be anchored against the peripheral distal wall of the meniscus tissue thereby maintaining the tear closed.

Optionally, the first and/or second apertures may be formed by two tubular needles of an applicator. The applicator may be similar to an applicator of the disclosed kits.

The method may then further include an optional step, according to which a tip of the first and/or second collapsible end portions is placed in the respective tubular needle of the applicator. In another optional step, the rod located within the respective tubular needle may be pushed distally in order to hold the first and/or second collapsible end portion against a distal rim of the opening of the respective tubular needle. Thus, the tip of the first and/or second collapsible end portion may be maintained in place while the first and/or second collapsible end portion is threaded through the first and/or second aperture. In a further optional step, when the applicator is in place (i.e., beyond the distal rim of the respective first or second aperture) the rod may be retracted proximally, thus letting the tip of the respective collapsible end portion out of the respective tubular needle through the opening of the respective tubular needle to lie beyond the distal rim of the respective first or second aperture (i.e., on a distal surface of the distal element).

The distal stretching of the second collapsible end portion may be performed by pushing the second tubular needle, which holds the tip of the second collapsible end portion (i.e., by its rod), distally until the bulge formed over the distal rim of the first aperture and the middle portion are brought closer to the distal rim of the first aperture and the proximal element, respectively.

Reference is now made to FIGS. 14A-14E which show top views of an applicator 670 deploying an implant 680 in a meniscus tissue 660 according to the method of FIG. 12 (or simply "the method"). Applicator 670 may be similar to applicator 400 of FIGS. 8A-8C. Implant 680 may be similar to implant 100 of FIG. 2. According to FIG. 14A, applicator 670 which includes a first tubular needle 675A and a second tubular needle 675B positioned in a housing 700 (i.e. retracted) may be positioned facing the concave side of a meniscus tissue 660. Meniscus tissue 660 includes a peripheral distal wall 710 and a proximal wall 715 with respect to applicator 670. Meniscus tissue 660 further includes a longitudinal tear 665.

According to FIG. 14B, tubular needle 675A may be projected from housing 700 (i.e., in an operative mode) and a first aperture may be formed in meniscus tissue 660 by tubular needle 675A through tear 665 according to step 600 of the method. Implant 680 (indicated in FIGS. 14C-14E) may be located in applicator 670. Collapsible end portion 685A of a flexible mesh tube of implant 680 (not indicated) may be located within tubular needle 675A. Thus, at the same time, collapsible end portion 685A may be threaded through the first aperture according to step 605 of the method.

According to FIG. 14C, tubular needle 675A may be retracted and thus position within housing 700. Collapsible end portion 685A may be collapsed therefore forming a bulge above a distal rim of the first aperture (not indicated), i.e. on peripheral distal wall 710. The bulge may be formed by pulling actuating element 705A of implant 680 according to step 610 of the method. Tubular needle 675B may be projected from housing 700 while a rod 690B maintains a collapsible end portion 685B of the flexible mesh tube in place within tubular needle 675B.

According to FIG. 14D, a second aperture may be formed in meniscus tissue 660 through tear 665 by tubular needle 675B according to step 615 of the method. At the same time, collapsible end portion 685B which may be maintained in tubular needle 675B may be threaded through the second aperture according to step 620 of the method. Tubular needle 675B and collapsible end portion 685B are positioned beyond peripheral distal wall 710. Pushing tubular needle 675B distally may stretch collapsible end portion 685B thus bringing the bulge above the distal rim of the first aperture closer to the distal rim and a middle portion 695 of the flexible mesh tube closer to proximal wall 715. The threading of collapsible end portion 685B (i.e., while collapsible end portion 685A is threaded and anchored) and the stretching of collapsible end portion 685B, may close tear 665.

According to FIG. 14E, tubular needles 675A and 675B are retracted and therefore positioned within housing 700. Collapsible end portion 685B may be collapsed therefore forming a bulge above a distal rim of the second aperture (not indicated), i.e. on peripheral distal wall 710. The bulge may be formed by pulling actuating element 705B of implant 680 according to step 625 of the method. Implant 680 may be then anchored in a fixed manner to meniscus tissue 660 and tear 665 may be maintained closed.

The disclosed devices and kits may be operated according to the above disclosed methods.

A further device is herein disclosed. The device may include a flexible tube and an actuating element. The flexible tube and the actuating element may be in the form and/or made similar to the flexible tube and the actuating element segments of the device disclosed herein above and referred by FIGS. 1-7F, respectively, with the modification described herein below. The flexible tube may include an end portion and a collapsible end portion. The end portion may include a first elongated hardened element located at a tip of the end portion. The collapsible end portion may include a second elongated hardened element threaded thereon. The actuating element may be secured to the collapsible end portion.

When the end portion and the collapsible end portion are threaded through two apertures, respectively, and the actuating element is pulled proximally, the collapsible end portion may collapse proximally and form a bulge in vicinity to the second elongated hardened element. A length dimension of the first elongated hardened element may be larger than the respective aperture. The bulge and a length dimension of the second elongated hardened element may be larger than the respective aperture. As a result of the above, the flexible tube may be anchored against a rim of each of the two apertures.

In some embodiments, the collapsible end portion may include a hardened tip and the actuating element may be secured to the hardened tip.

Figure 15A:
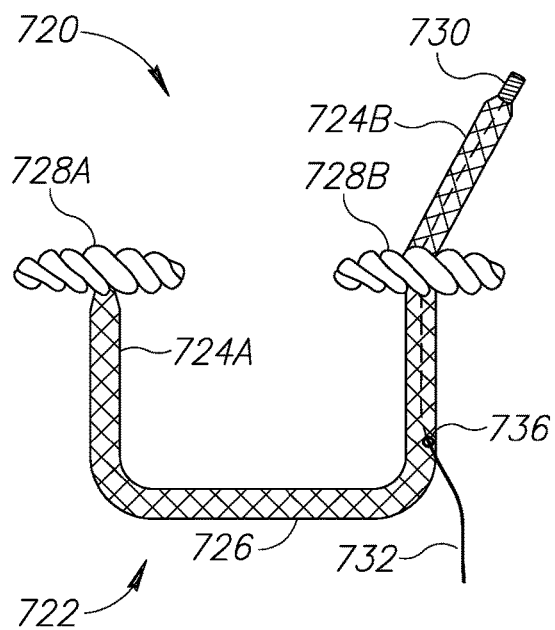
FIGS. 15A and 15B show side views of an exemplary device including a flexible mesh tube arranged in a U-shape, where the flexible mesh tube includes two elongated hardened elements, in a non-collapsed mode and in a collapsed mode, respectively.
Figure 15B:
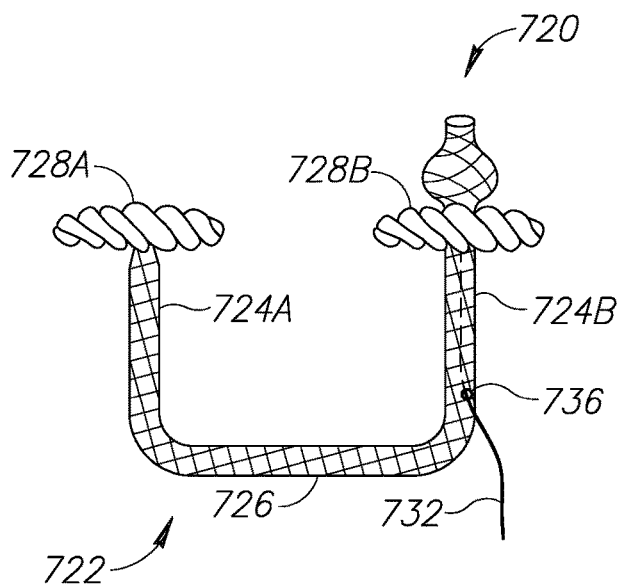

Reference is now made to FIGS. 15A and 15B, which show side views of an exemplary device 720 including a flexible mesh tube 722 arranged in a U-shape, where flexible mesh tube 722 includes two elongated hardened elements, in a non-collapsed mode and in a collapsed mode, respectively.

Device 720 may include flexible mesh tube 722 and an actuating element 732. Flexible mesh tube 722 may include an end portion 724A, a collapsible end portion 724B and a middle portion 726 there between. End portion 724A may include an elongated hardened element 728A. Collapsible end portion 724B may include an elongated hardened element 728A threaded thereon. Optionally, collapsible end portion 724B may include a hardened tip 730 and an opening 736 through which actuating element, which may extend along an inner void of collapsible end portion 724B, may exit the flexible mesh tube.

Device 720 is arranged in the FIGS. 15A and 15B in a U-shape, which may be the operative arrangement of device 720, i.e., the arrangement of device 720 when it is deployed. End portion 724A may be threaded through a first aperture and collapsible end portion 724B may be threaded through a second aperture, such that each elongated hardened element 728A and 728B is located distally with respect to a distal rim of the respective aperture. Actuating element 723 may be then pulled proximally thus collapsing collapsible end portion 724B to form a bulge in vicinity to elongated hardened element 728B, for example, on elongated hardened element 728B, as shown in FIG. 15B. Thereby device 720 may be anchored to a distal rim of each of the apertures.

Figure 16A:
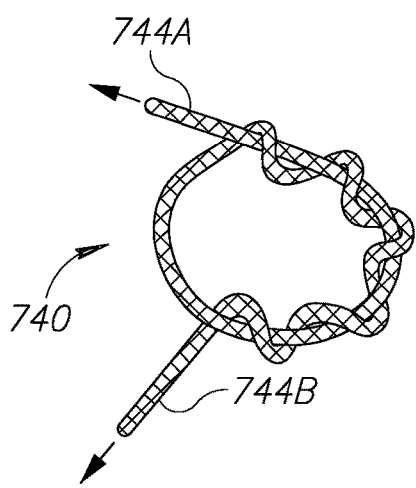
FIG. 16A shows a perspective view of a thread when twisted on itself to form an involute elongated hardened element.
Figure 16B:
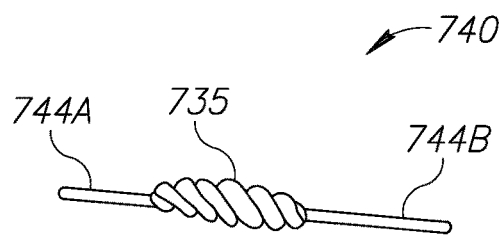
FIG. 16B shows a side view the thread of FIG. 16A including the involute elongated hardened element.

In some embodiments, the first and second elongated hardened elements may have an involute shape, such as elongated hardened elements 728A and 728B. Reference is now made to FIGS. 16A and 16B. FIG. 16A shows a perspective view of a thread 740 when twisted around itself to form an involute elongated hardened element. FIG. 16B shows a side view of thread 740 of FIG. 16A including an involute elongated hardened element 735. Involute elongated hardened element 735 may be formed by an elongated and flexible element, such as a thread 740. An end portion 744B of thread 740 may be twisted around an end portion 744A of thread 740, as shown in FIG. 16A, in order to form an elongated hardened element which is involute. FIG. 16B shows thread 740 when arranged to include involute hardened element 732 between a remainder of each of end portions 744A and 744B. The remainder may be then removed.

In some embodiments, the first and second elongated hardened elements may be made of polymer. Reference is now made to FIGS. 17A-17C. FIG. 17A shows a cross-section of an elongated hardened element 758 including a bore and made of polymer. FIG. 17B shows a cross-section of an exemplary device 750 including two elongated hardened elements such as elongated hardened element 758 of FIG. 17A and arranged in a U-shape. FIG. 17C shows a collapsible end portion of a flexible mesh tube of device 750 of FIG. 17B, when collapsed. Elongated hardened element 758 may be made of polymer. Elongated hardened element 758 may include a bore 760, through which a flexible tube of the disclosed device may be threaded.

Exemplary device 750 may be similar to device 720 of FIGS. 15A and 15B with the modification described herein below. Device 750 may include a flexible mesh tube 752 and an actuating element 762. Flexible mesh tube 752 may include an end portion 754A, a collapsible end portion 754B and a middle portion 756 there between. An end portion 754A may include a hardened elongated element 758A. Optionally, end portion 754A may include a thickened end 762. Collapsible end portion 754B may include a hardened elongated element 758B. Optionally, collapsible end portion 754B may include a hardened end 764. Hardened elongated element 758A and hardened elongated element 758B may be similar to elongated hardened element 758 of FIG. 17A.

Thus, each of hardened elongated element 758A and hardened elongated element 758B may include a bore 760A and 760B, respectively, through which each of end portion 754A and collapsible end portion 754B are threaded, respectively. Thickened end 762 may be used to anchor end portion against hardened elongated element 758A. Actuating element may be secured to hardened tip 764, extend within collapsible end portion 754B and exit flexible mesh tube 752 through an opening 766. When actuating element 762 is pulled proximally, Collapsible end portion may collapse proximally therefore forming a bulge in vicinity to hardened elongated element 758B. Hardened elongated element 758B may include a length dimension larger than a second aperture through which collapsible end portion 754B may be threaded. In addition, the bulge may be larger than bore 760B, as shown in FIG. 17C. Thus, flexible mesh tube 752 may be anchored against a distal rim of the second aperture.

In some embodiments, the disclosed devices may be used for repairing a tear in a meniscus tissue. The end portion and the collapsible end portion may be threaded through two apertures, respectively, made in the meniscus tissue through the tear in order to bring two edges of the tear closer together. When the actuating element segment is pulled proximally, the flexible tube may be anchored against a peripheral distal wall of the meniscus tissue thereby maintaining the tear closed.

Kits for repairing a tear in a meniscus tissue are disclosed herein. Reference is now made to Fig.18A, which shows a top transparent view of an exemplary kit 770 including an applicator 772 and an implant 774. Applicator 772 may be similar to applicator 400 of FIGS. 8A-8C and/or applicator 500 of FIG. 10, with the modifications disclosed herein below. Implant 774 may be similar to implant 860 of FIGS. 14A-14E with the modifications disclosed herein below. Implant 774 may include a flexible tube such as a flexible mesh tube 775 and an actuating element 782. Flexible mesh tube 775 may include an end portion 776A and a collapsible end portion 776B. End portion 776A may include a first elongated hardened element 778A. Collapsible end portion 776B may include a second elongated hardened element 778B. Optionally, collapsible end portion 776B may include a hardened tip 784

Actuating element 782 may be secured to collapsible end portion 778B, and optionally to hardened tip 784. First elongated hardened element 778A may be located at a tip of end portion 776A. Second elongated hardened element 778B may be threaded on collapsible end portion 776B. Optionally, first and second elongated hardened elements 778A and 778B may be involute. Optionally, first and second elongated hardened elements 778A and 778B may be made of polymer and/or may be similar to elongated hardened elements 758A and 758B of FIGS. 17A-17C.

Applicator 772 may include a first tubular needle 782A and a second tubular needle 782B. First tubular needle 782A may include a first rod 783A and a first opening 781A. Second tubular needle 782B may include a second rod 783B and a second opening 781B. First rod 783A and second rod 783B may be positioned within first tubular needle 782A and second tubular needle 782B, respectively. First rod 783A may include a graded tip. Second rod 783B may include a recess at its tip. Alternatively or additionally, applicator 772 may include an opening which may be located laterally with respect and in each of tubular needles 782A and 782B (i.e., a first and a second lateral opening, not shown in this view).

End portion 776A and collapsible end portion 776B may be threaded through two apertures by applicator 772, respectively. First tubular needle 782A may be configured to puncture the meniscus tissue to form a respective aperture. First opening 781A or the lateral opening may be configured to allow insertion of first elongated hardened element 778A into first tubular needle 782A. First rod 783A may be configured to maintain a first elongated hardened element 778A in place within first tubular needle 782A. Second tubular needle 782B may be configured to puncture the meniscus tissue to form a respective aperture. Second opening 781B or the second lateral opening may be configured to allow insertion of second elongated hardened element 778B and collapsible end portion 776B into second tubular needle 782B. Second rod 783B may be configured to maintain second elongated hardened element 778B and collapsible end portion 776B in place within second tubular needle 782B. The recess of second rod 783B may be configured to accommodate hardened tip 784.

Actuating element 782 may be then pulled proximally. As a result of that, collapsible end portion 776B may collapse proximally and form a bulge in vicinity to second elongated hardened element 778B. A length dimension of first elongated hardened element 778A may be larger than the respective aperture. The bulge and a length dimension of second elongated hardened element 778B may be larger than the respective aperture, thereby anchoring flexible mesh tube 775 against a peripheral distal wall of the meniscus tissue.

Alternatively, any applicator known in the art may be used in order to deploy implant 774 in the meniscus tissue by puncturing the meniscus tissue to form two apertures passing through the tear and threading end portion 778A and collapsible end portion 778B through the two apertures, respectively.

In some embodiments, kit 770 may include an applicator which includes only one tubular needle configured to deploy implant 772 in the meniscus tissue. The applicator may be similar to applicator 560 of FIG. 11 and/or to applicator 772 of FIG. 18A, with modification as disclosed below.

Reference is now made to Fig.18B, which shows a top transparent view of another exemplary kit 790 including an applicator 794 and an implant 792. Applicator 784 may include a tubular needle 802. Tubular needle 802 may include an opening, which may be front opening 803 and/or a lateral opening (not shown) and a rod (both not shown in this view). Implant 792 may be similar to implant 775 of FIG. 18A. Implant 792 may include a flexible mesh tube 804 and an actuating element 800. Flexible mesh tube 804 may include an end portion 796A and a collapsible end portion 796B. End portion 796A may include a first elongated hardened element 798A located at a tip of end portion 796A. Collapsible end portion 796B may include a second elongated hardened element 798B threaded thereon.

Front opening 803 may be configured to allow insertion of flexible mesh tube 804 into tubular needle 802. The rod may be positioned within tubular needle 802 and may be configured to maintain flexible mesh tube 804 in place within the tubular needle Tubular needle 802 may be configured to puncture the meniscus tissue to form the two apertures and deploy implant 792 in the meniscus tissue.

In an alternative applicator (not shown), two elongated hardened elements may be positioned within a pair of suitable side grooves inside an elongated needle. These grooves may be disposed sequentially along the length of the elongated needle.

Figure 19:
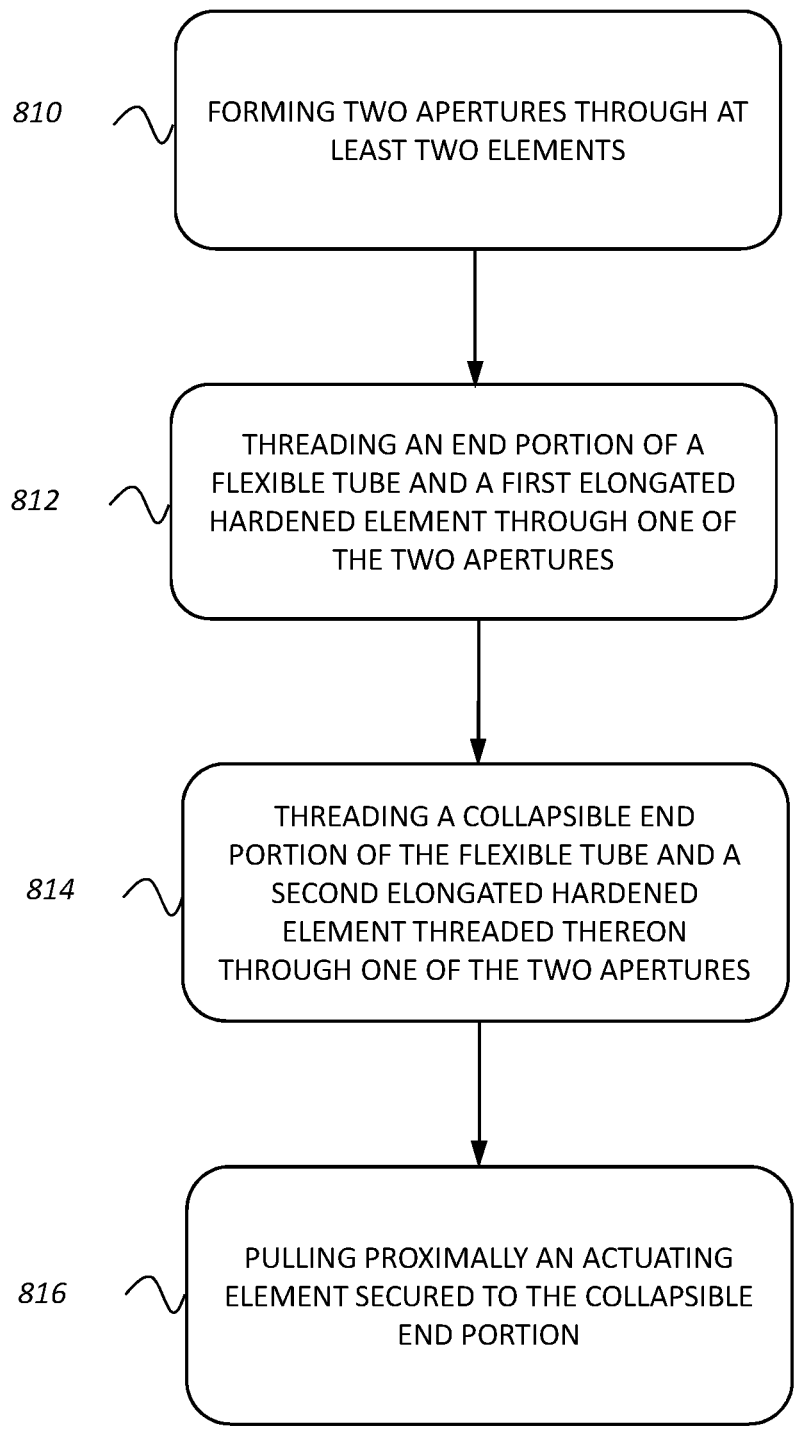
FIG. 19 shows a flowchart of another method for joining at least two elements, constructed and operative in accordance with an embodiment of the disclosed technique.

Reference is now made to FIG. 19, which shows a flowchart of another method for joining at least two elements, constructed and operative in accordance with an embodiment of the disclosed technique. The method may be similar to the method of FIG. 12 with modifications as described below. In a step 810, two apertures may be formed through the at least two elements. The apertures may be formed in the two or more elements by entering through the most proximal element, passing through all of the other elements to be joined and exiting through the most distal element.

In a step 812, an end portion of a flexible tube and a first elongated hardened element located at a tip of the end portion may be threaded through a respective aperture of the apertures, entering through the most proximal element and exiting through the most distal element. The first elongated hardened element may be then placed beyond a distal rim of the respective aperture (i.e., on a distal surface of the most distal element). The flexible tube may be similar to the flexible tube of the disclosed devices.

In a step 814, a collapsible end portion of the flexible tube and a second elongated hardened element threaded thereon may be threaded through a respective aperture of the apertures, entering through the most proximal element and exiting through the most distal element. The second elongated hardened element and at least a section of the collapsible end portion extending distally there from may be placed beyond a distal rim of the respective aperture (i.e., on a distal surface of the most distal element).

Optionally, each of the first and second elongated hardened elements may have an involute shape. Optionally, each of the first and second elongated hardened elements may be made of polymer. Optionally, the collapsible end portion may include a hardened tip. The actuating element may be secured to the hardened tip, advantageously to a center of a bottom surface of the hardened tip, as shown in FIGS. 15A-15B.

In a step 816, an actuating element secured to the collapsible end portion and extending along the collapsible end portion may be pulled proximally. The section of the collapsible end portion may then collapse proximally and form a bulge in vicinity to the second elongated hardened element. A length dimension of the first elongated hardened element may be larger than the respective aperture. The bulge and a length dimension of the second elongated hardened element may be larger than the respective aperture. Thus, the flexible tube may be anchored against the distal rim of each one of the two apertures (i.e., against the distal surface of the most distal element).

In case the at least two elements are separable, they may be arranged to assure firm and effective joining of the two or more elements. The location of the entrance of the first and/or second aperture in the most proximal element and/or the path of the first and/or second apertures through the other elements may be selected to assure firm and effective joining of the two or more elements.

In a further optional step, the collapsible end portion may be stretched distally, thereby bringing the bulge formed over the distal rim of the respective aperture closer to the distal rim and a middle portion of the flexible tube closer to the most proximal element (i.e., a proximal surface of the most proximal element). Thus, tightening the joining of the two or more elements.

In some embodiments, the disclosed methods may be used for repairing a tear in a meniscus tissue. The method may then use the disclosed devices and kits for repairing a tear in a meniscus tissue. In such a case, the two or more elements to be joined may include a peripheral distal wall of the meniscus tissue and a proximal wall of the meniscus tissue. The end portion and the first elongated hardened element may be threaded through a first aperture made in the meniscus tissue through the tear. The collapsible end portion and the second elongated hardened element may be threaded through a second aperture made in the meniscus tissue through the tear. Thereby bringing two edges of the tear closer together. When the actuating element is pulled proximally, the flexible tube may be anchored against the peripheral distal wall of the meniscus tissue thus maintaining the tear closed.

Optionally, the first and second apertures may be formed by a first and a second tubular needle of an applicator. The applicator may be similar to an applicator of the disclosed kits.

The method may then further include an optional step, according to which the first elongated hardened element may be placed in the first tubular needle of the applicator parallelly with respect to the first tubular needle.

In another optional step, the collapsible end portion and the second elongated hardened element may be placed in the second tubular needle of the applicator. The second elongated hardened element may be placed parallelly with respect to the second tubular needle.

In a further optional step, a first rod located within the first tubular needle may be pushed distally in order to hold the end portion against a distal rim of a first lateral opening of the first tubular needle.

In another optional step, a second rod located within the second tubular needle may be pushed distally in order to hold the flexible tube against a distal rim of a second lateral opening of the second tubular needle. Thus, the first elongated hardened element and the collapsible end portion and the second elongated hardened element may be maintained in place, respectively, while the end portion and the collapsible end portion are threaded through the first and second apertures, respectively.

In a further optional step, when the first needle is in place (i.e., beyond the distal rim of the first aperture), the first rod may be retracted proximally, thus letting the first elongated hardened element out of the first tubular needle through the first lateral opening to lie beyond the distal rim of the first aperture (i.e., on a distal surface of the peripheral distal wall). Alternatively, the first rod may be pushed distally, thus letting the first elongated hardened element out of the first tubular needle through a first top opening to lie beyond the distal rim of the first aperture (i.e., on a distal surface of the peripheral distal wall).

In another optional step when the second needle is in place (i.e., beyond the distal rim of the second aperture) the second rod may be retracted proximally. Thus, letting the second elongated hardened element and at least an end section of the collapsible end portion extending from the second elongated hardened element out of the second tubular needle through the second lateral opening. Alternatively, the second rod may be pushed distally. Thus, letting the second elongated hardened element and at least an end section of the collapsible end portion extending from the second elongated hardened element out of the second tubular needle through the second top opening. The second elongated hardened element and at least the end section may then lie beyond the distal rim of the second aperture (i.e., on a distal surface of the peripheral distal wall).

The distal stretching of the second collapsible end portion may be performed by pushing the second tubular needle, which holds the second elongated hardened element and at least an end section of the collapsible end portion (i.e., by the second rod), distally. This may be performed in order to bring the first elongated hardened element located over the distal rim of the first aperture closer to the distal rim of the first aperture and to bring the middle portion of the flexible tube closer to the proximal wall, respectively, thereby further closing the tear.

Optionally, each of the first and second elongated hardened elements may have an involute shape. Optionally, each of the first and second elongated hardened elements may be made of polymer. Optionally, the collapsible end portion may include a hardened tip and the actuating element may be secured to the hardened tip.

Reference is now made to FIGS. 20A-20G, which show top views, partially transparent, of an applicator 820 deploying an implant 822 in a meniscus tissue 826 according to the method of FIG. 19 (or simply "the method"). Applicator 820 may be similar to applicator 772 of FIG. 18A. Implant 822 may be similar to implant 774 of FIG. 18A. According to FIG. 20A, Applicator 820 may be positioned facing the concave side of meniscus tissue 826. Applicator 820 may include a first tubular needle 830A and a second tubular needle 830B. First tubular needle 830A may be projected from a housing 832 (i.e., in an operative mode) and second tubular needle 830B may be located in housing 832 (i.e., in a non-operative mode). An elongated hardened element 838B and at least an end section of a collapsible end portion 836B are maintained within tubular needle 830B by a rod 834B (show in FIG. 20D). A rod 834A positioned within tubular needle 830A may be pushed proximally in order to maintain an elongated hardened element 83 8A within a tubular needle 830A. Rod 830A may include a graded tip 846. Meniscus tissue 826 may include a peripheral distal wall 848 and a proximal wall 850 with respect to applicator 820. Meniscus tissue 826 may further include a longitudinal tear 828.

Figure 20A:
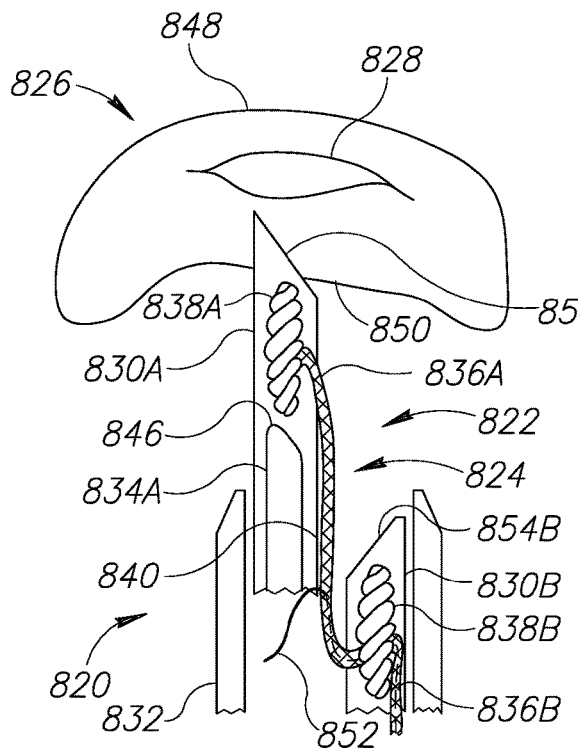
FIGS. 20A-20H show top views, partially transparent, of an applicator deploying an implant in a meniscus tissue according to the method of FIG. 19.
Figure 20B:
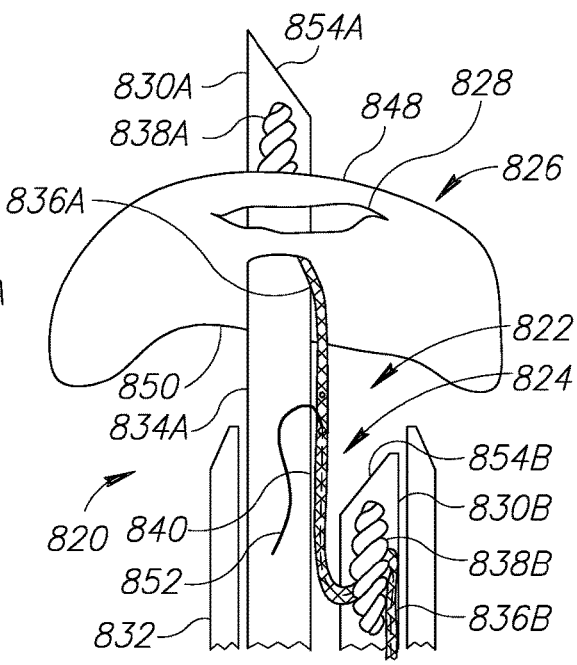

According to FIG. 20B, tubular needle 830A may puncture meniscus tissue 826 at proximal wall 850 to form a first aperture through tear 828 according to step 810 of the method. Therefore, threading elongated hardened element 838A and following that, an end portion 836A of mesh flexible tube 824 of implant 822, through the first aperture, according to step 812 of the method.

Figure 20C:
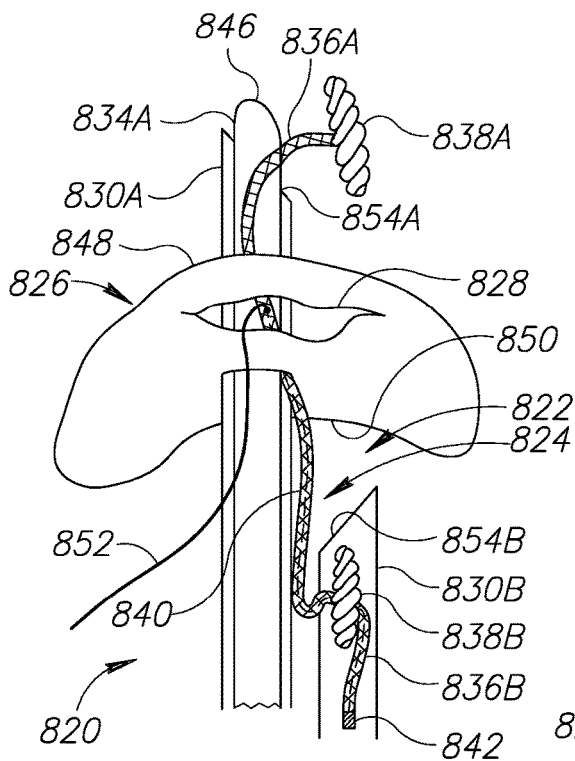

According to FIG. 20C, rod 834A may push elongated hardened element 838A through a top aperture 854A of tubular needle 830A out of tubular needle 830A. Alternatively, rod 834A may be retracted proximally, thus letting elongated hardened element 838A out through a lateral aperture (not shown) of tubular needle 830A.

Figure 20D:
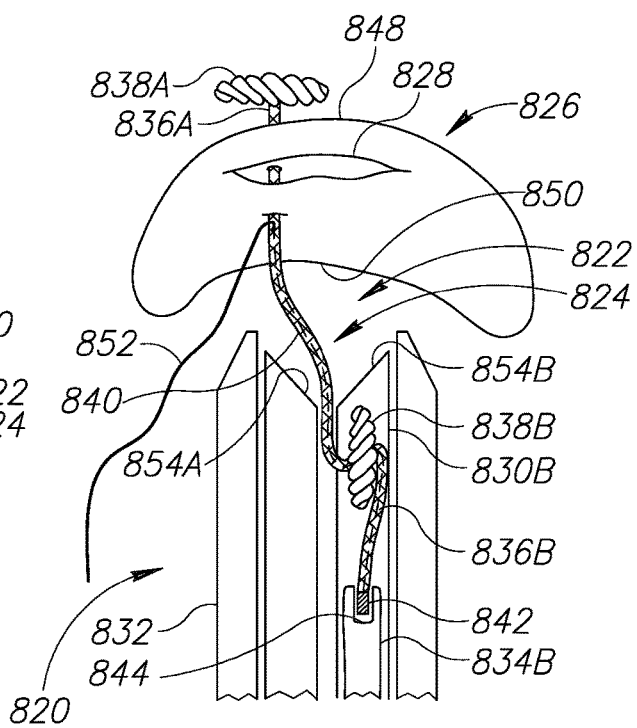

According to FIG. 20D, tubular needle 830A may be retracted and thus position within housing 832. Elongated hardened element 838A may be placed above a distal rim of the first aperture (not indicated), i.e. on peripheral distal wall 848.

Figure 20E:
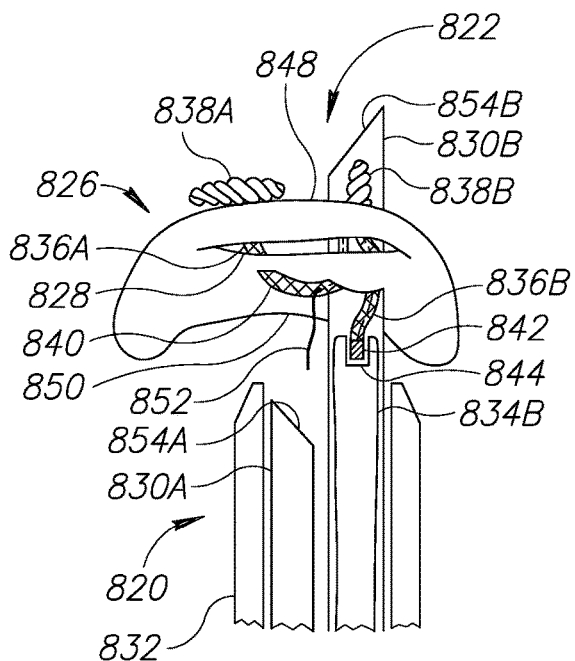

According to FIG. 20E, a second aperture may be formed in meniscus tissue 826 through tear 828 by tubular needle 830B according to step 810 of the method. At the same time, elongated hardened element 838B and collapsible end portion 836B maintained in tubular needle 830B may be threaded through the second aperture according to step 814 of the method.

Figure 20F:
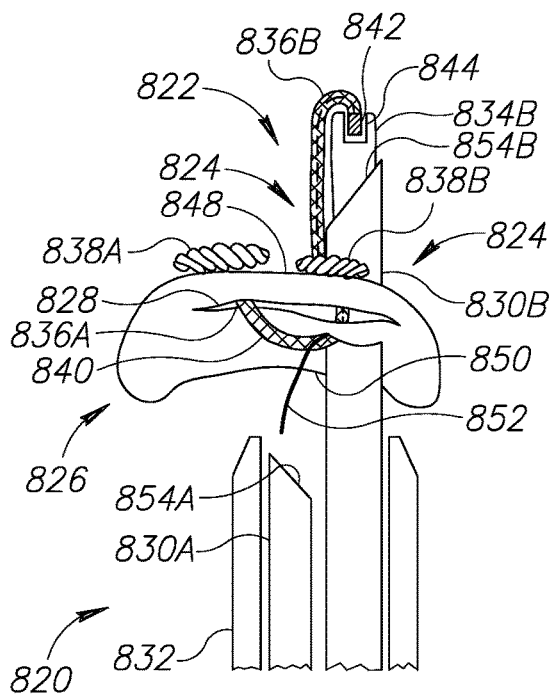

According to FIG. 20F, rod 834B may be pushed distally in order to push elongated hardened element 838B out of tubular needle 830B. Alternatively, rod 834B may be retracted proximally, thus letting elongated hardened element 838B and collapsible end portion 836B out through a lateral aperture (not shown) of tubular needle 830B. Pushing rod 834B distally may further stretch flexible mesh tube 822, thereby bringing the bulge formed over the distal rim of the first aperture closer to the distal rim and middle portion 840 closer to proximal wall 850 (i.e., a proximal surface of proximal wall 850). Thus, tightening the joining of the edges of tear 828 (i.e., closing tear 828).

Figure 20G:
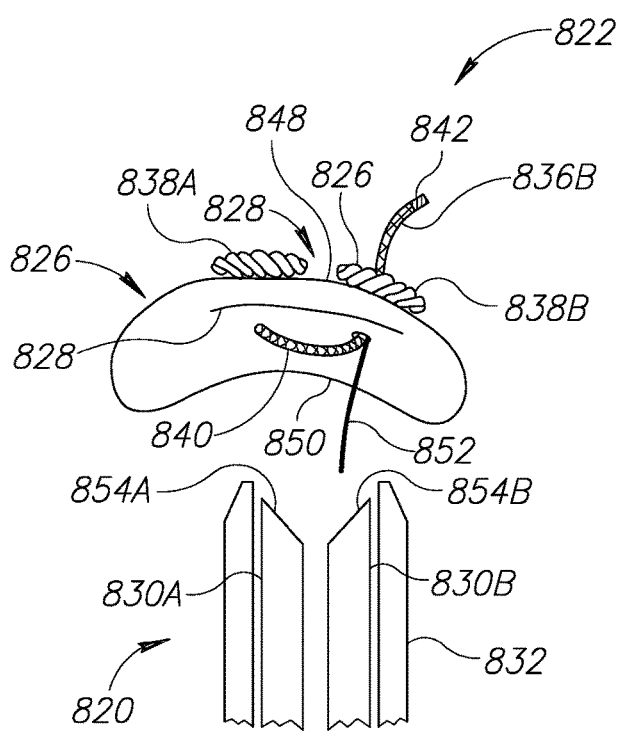

According to FIG. 20G, tubular needle 830B may be retracted and therefore positioned within housing 832, while leaving elongated hardened element 838B and collapsible end portion 836B lying beyond the distal rim of the second aperture.

Figure 20H:
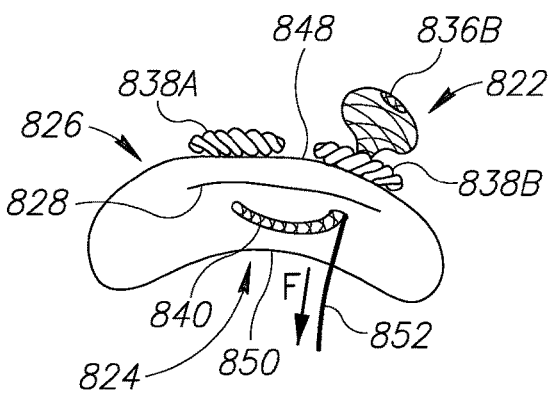

According to FIG. 20H, an actuating element 852 of implant 822 may be pulled proximally according to step 816 of the method. (the direction of the pulling is indicated by an arrow and the letter "F"). As a result of that, collapsible end portion 836B may be collapsed therefore forming a bulge above a distal rim of the second aperture (not indicated), i.e. on peripheral distal wall 848. Implant 822 may be then anchored in a fixed manner to meniscus tissue 826 and tear 828 may be maintained closed.

A further device is herein disclosed. The device may include a flexible tube and an actuating element. The flexible tube and the actuating element may be in the form and/or made similar to the flexible tube and the actuating element segments of the devices disclosed herein above, with the modification described herein below. The flexible tube may include a first and a second end portion. The first end portion may include a first elongated hardened element located at a tip of the end portion. The second end portion may include a second elongated hardened element threaded thereon, a pulling anchor located along the second end portion and a collapsible segment extending from the pulling anchor towards a middle portion of the flexible tube. The actuating element may be secured to the pulling anchor and extend therefrom along the second end portion towards the middle portion of the flexible tube.

When the first end portion is threaded through a first aperture, and the second end portion is threaded back and forth, at least once, through a second aperture, and such that the second elongated hardened element and the pulling anchor are located at different sides with respect to the second aperture, the actuating element may be pulled proximally. As a result, the collapsible segment of the second end portion may collapse towards the second elongated hardened element and form a bulge larger than the second aperture. In addition, the first aperture may be smaller than a length dimension of the first elongated hardened element and the second aperture smaller than a length dimension of the second elongated hardened element. Thus, the flexible tube may be anchored against a rim of the first aperture and two rims at two sides of the second aperture.

The first and second elongated hardened elements may be similar to the elongated hardened elements of the above disclosed devices, as described, for example, with respect to FIGS. 15A-17C. Optionally, each of the first and second elongated hardened elements may have an involute shape. Optionally, each of the first and second elongated hardened elements may be made of polymer.

Figure 21A:
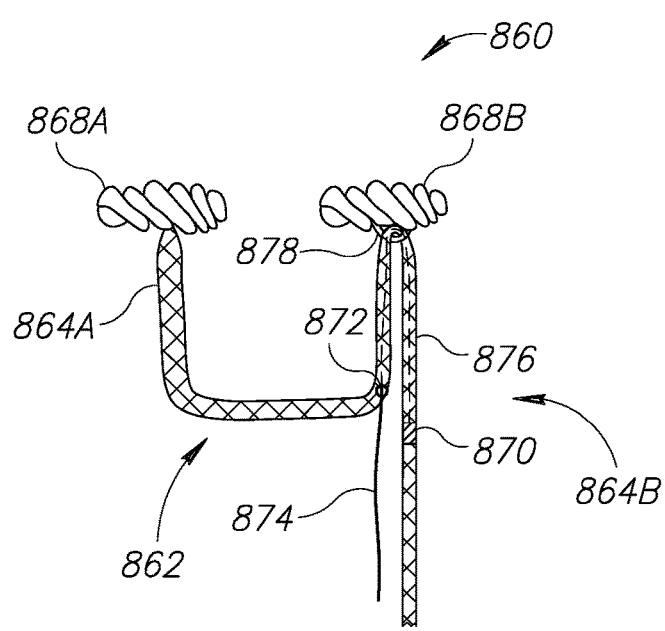
FIG. 21A shows a side view of a device when it is arranged in a U shape.
Figure 21B:
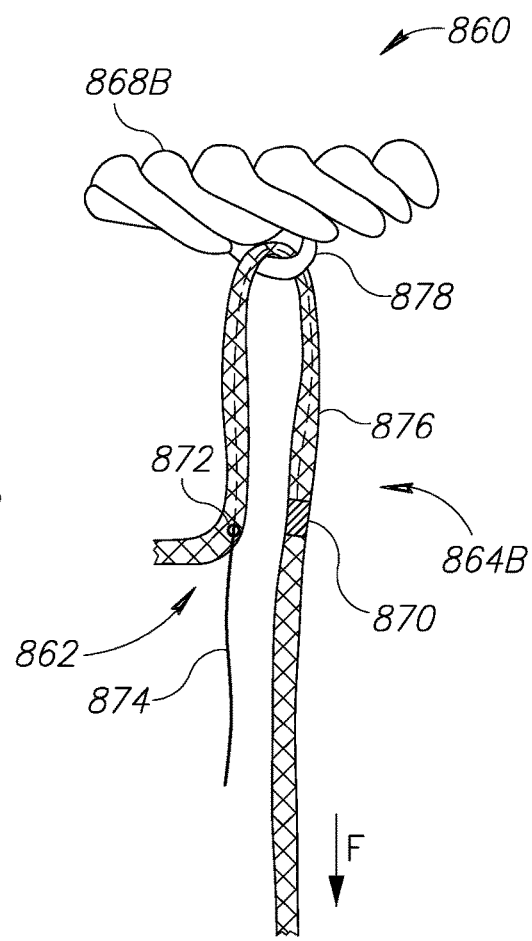
FIG. 21B shows a side view of a portion of the device of FIG. 21A including the second end portion of a flexible mesh tube of the device and an actuating element of the device.

Reference is now made to FIGS. 21A and 21B. FIG. 21A shows a side view of a device 860 when it is arranged in a U-shape. FIG. 21A shows a side view of a portion of device 860 of FIG. 21A including a second end portion of a flexible mesh tube of device 860 and an actuating element of the device. Device 860 may include a flexible mesh tube 862 and an actuating element 874. Flexible mesh tube 862 may include a first end portion 864A, a second end portion 864B and a middle portion 866. First end portion 864A may include a first elongated hardened element 868A. Second end portion 864B may include a second elongated hardened element 868B, a pulling anchor 870 and a collapsible segment 876. Flexible mesh tube 862 may further include an aperture 872. First elongated hardened element 868A may be located at a tip of first end portion 864A. Second elongated hardened element 868B may be threaded on second end portion 864B, e.g., by a loop 878. Actuating element 874 may be secured to pulling anchor 870 and may extend therefrom along second end portion 864B towards middle portion 866. Actuating element 874 may exit flexible mesh tube 862 through an aperture 872. Collapsible segment 876 may extend from pulling anchor 870 towards middle portion 866.

Pulling anchor 870 may be formed by melting flexible mesh tube 862 and/or by over-molding, as discussed above. Alternatively, pulling anchor 870 and any other pulling anchor of the specification may be formed by any other technique for localized circumferential narrowing of flexible mesh tube 862, such as by deploying a ring, a belt, a thread and/or the like around the flexible mesh tube.

In some embodiments, the disclosed devices may be used for repairing a tear in a meniscus tissue. The first and second end portions may be threaded through two apertures, respectively, made in the meniscus tissue through the tear in order to bring two edges of the tear closer together. When the actuating element segment is pulled proximally, the flexible tube may be anchored against a peripheral distal wall and a proximal wall of the meniscus tissue thereby maintaining the tear closed.

A kit for repairing a tear in a meniscus tissue is herein disclosed. The kit may include and implant, similar to implant 860 of FIGS. 21A and 21B, and an applicator. The applicator may be configured to deploy the implant in the meniscus tissue by puncturing the meniscus tissue to form two apertures passing through the tear and threading the first end portion and the second end portion of the flexible mesh tube of the implant through the two apertures, respectively. The applicator may be similar to applicator 770 of FIG. 18A or applicator 790 of FIG. 18B.

The first end portion may be threaded through a first aperture and the second end portion may be threaded back and forth, at least once, through a second aperture, by the applicator. The threading may be performed such that the second elongated hardened element and the pulling anchor are located at different sides with respect to the second aperture. The actuating element may be then pulled proximally. As a result, the collapsible segment of the second end portion may collapse towards the second elongated hardened element and form a bulge larger than the second aperture. In addition, the first aperture may be smaller than a length dimension of the first elongated hardened element and the second aperture smaller than a length dimension of the second elongated hardened element. Thus, the flexible tube may be anchored against a rim of the first aperture and two rims at two sides of the second aperture.

Figure 22:
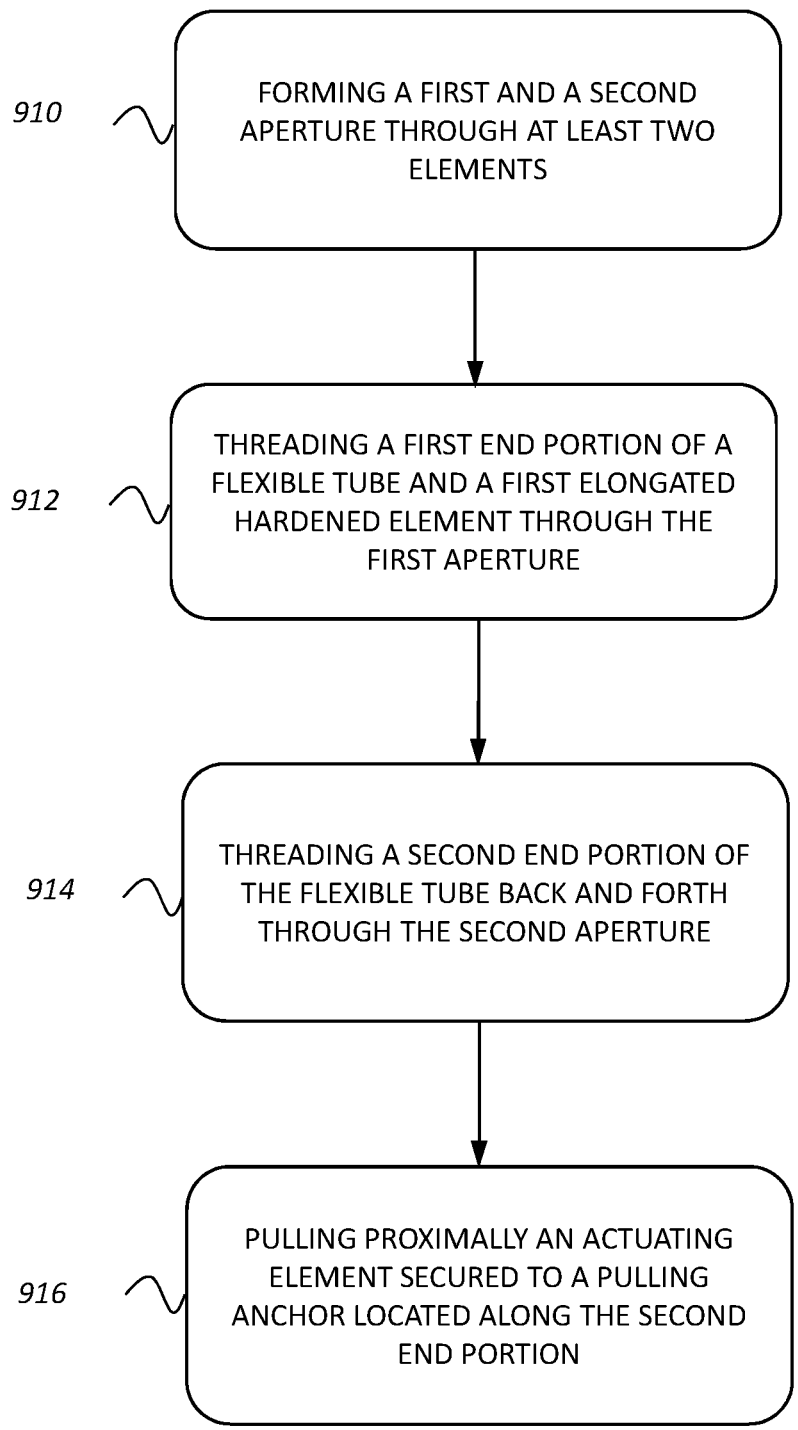
FIG. 22 shows a flowchart of a further method for joining at least two elements, constructed and operative in accordance with an embodiment of the disclosed technique.

Reference is now made to FIG. 22, which shows a flowchart of a further method for joining at least two elements, constructed and operative in accordance with an embodiment of the disclosed technique. In a step 910, a first and a second aperture passing through the at least two elements may be formed.

In a step 902, a first end portion of a flexible tube and a first elongated hardened element located at a tip of the first end portion may be threaded through the first aperture. The first elongated hardened element may be then placed beyond a distal rim of the first aperture.

In a step 914, a second end portion of the flexible tube may be threaded back and forth through the second aperture. A second elongated hardened element threaded on the second end portion and a pulling anchor located along the second end portion may be then placed at different sides with respect to the second aperture.

In a step 916, an actuating element secured to the pulling anchor and extending along the second end portion may be pulled proximally. As a result of that, a collapsible segment of the second end portion, extending from the pulling anchor towards a middle portion of the flexible tube, may collapse towards the second elongated hardened element and form a bulge larger than the second aperture. A length dimension of the first elongated hardened element may be larger than the first aperture, and a length dimension of the second elongated hardened element may be larger than the second aperture, thereby anchoring the flexible tube to the two elements.

In some embodiments, the disclosed method may be used for repairing a tear in a meniscus tissue. The method may then use the disclosed devices and kits for repairing a tear in a meniscus tissue. In such a case, the two or more elements to be joined may include a peripheral distal wall of the meniscus tissue and a proximal wall of the meniscus tissue. The first end portion and the first elongated hardened element may be threaded through a first aperture made in the meniscus tissue through the tear. The second end portion and the second elongated hardened element may be threaded through a second aperture made in the meniscus tissue through the tear. Thereby bringing two edges of the tear closer together. When the actuating element is pulled proximally, the flexible tube may be anchored against the peripheral distal wall and the proximal wall of the meniscus tissue thus maintaining the tear closed.

Reference is now made to FIGS. 23A-23E, which show side and perspective views of an implant 880 deployed in a meniscus tissue 896 according to the method of FIG. 22.

Figure 23A:
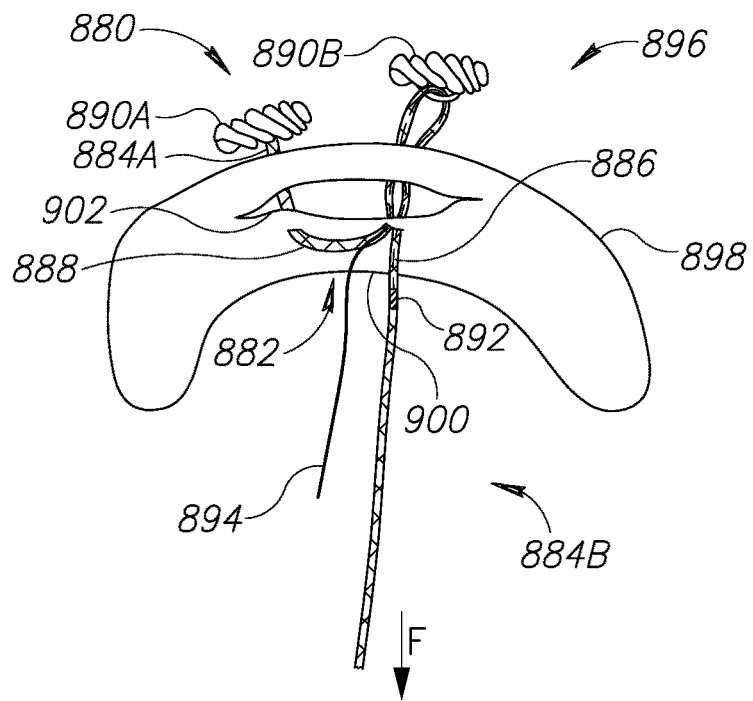

According to FIG. 23A, a meniscus tissue 896 may be punctured in two locations in a proximal wall 900 of meniscus tissue 896 to form a first and a second apertures passing through a tear 902 in meniscus tissue 896 and exiting meniscus tissue 896 through a peripheral distal wall 898 of meniscus tissue 896, according to step 910 of the method. The puncturing may be performed by an applicator of the disclosed kits.

A first end portion 884A of a flexible tube 882 of implant 880 and a first elongated hardened element 890A located at a tip of first end portion 884A may be threaded through the first aperture by the applicator. Advantageously, while puncturing meniscus tissue 896. First elongated hardened element 890A may be placed beyond peripheral distal wall 898. A second end portion 884B of flexible tube 882 of implant 880 may be threaded back and forth through the second aperture by the applicator. A second elongated hardened element 890B, threaded on second end portion 884B, and a pulling anchor 870 located along second end portion 884B, may be placed at different sides with respect to the second aperture (i.e., one beyond peripheral distal wall 898 and the other before proximal wall 900).

Figure 23B:
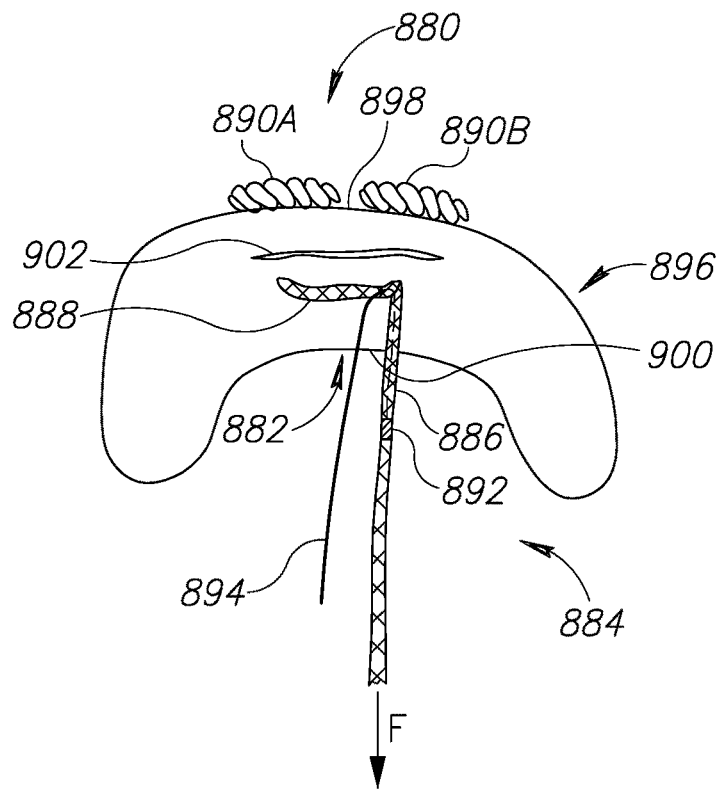

According to FIG. 23B, end portion 884 may be stretched proximally (the direction of pulling is indicated by an arrow and the letter "F") in order to close tear 902 by bringing elongated hardened element 890A closer to a distal rim of the first aperture, middle portion 900 closer to proximal wall 900 and elongated hardened element 890B closer to a distal rim of the second aperture.

According to FIG. 23C and 23D, an actuating element 894 of implant 860 may be pulled proximally (the pulling direction is indicated by an arrow and the letter "F"). Actuating element 894 may be secured to pulling anchor 892 and may extend along second end portion 884B. As a result of that, collapsible segment 886 of second end portion 884B, extending from pulling anchor 892 towards middle portion 866 of flexible tube 862, may collapse towards second elongated hardened element 890B and form a bulge. The bulge may be larger than the second aperture. Optionally, the bulge may be of a size such that to allow the bulge to enter the second aperture and stopped there within.

According to FIG. 23E, flexible tube 882 and therefore implant 880 may be firmly anchored to meniscus tissue 896. This may be achieved since a length dimension of first elongated hardened element 890A may be larger than the first aperture, and a length dimension of second elongated hardened element 890B may be larger than the second aperture.

A flexible tube according to the disclosed devices, kits and methods, which may be used in medical procedures, may be made of materials such as polyester (for example, DYNEEMA®, by Koninklijke DSM N.V. of TE Heerlen, Netherlands), nylon or a medical suture. The flexible mesh tube may be formed by braiding, knitting or weaving. A length of a flexible tube according to the disclosed devices, kits and methods for repairing a meniscus tissue may range between 8 to 55 millimeters, 20 to 40 millimeters, 25 to 35 millimeters, 8 to 20 millimeters or 40 to 55 millimeters. A diameter of a bulge formed by a portion of a flexible tube according to the disclosed devices, kits and methods used in medical procedures may be between 1 to 8 millimeters, 3 to 7 millimeters, 5 to 6 millimeters, 1 to 3 millimeters or 6 to 8 millimeters.

An actuating element or an actuating element segment according to the disclosed devices, kits and methods, which may be used in medical procedures, may be made of materials such as polyester (for example, DYNEEMA®), nylon or a suture. A length of an actuating element or an actuating element segment according to the disclosed devices, kits and methods for repairing a meniscus tissue may range between 8 to 55 millimeters, 20 to 40 millimeters, 25 to 35 millimeters, 8 to 20 millimeters or 40 to 55 millimeters. A thickness of an actuating element or an actuating element segment according to the disclosed devices, kits and methods used in medical procedures for joining soft tissues may range between 0.05 to 1.2 millimeter, 0.3 to 1.0 millimeters, 0.5 to 0.8 millimeters, 0.1 to 0.3 millimeters or 0.8 to 1.2 millimeters. A thickness of an actuating element or an actuating element segment according to the disclosed devices, kits and methods used in medical procedures for joining sclerous tissues may range between 1 to 17 millimeter, 5 to 14 millimeters, 8 to 11 millimeters, 1 to 4 millimeters or 13 to 17 millimeters.

A volute elongated hardened element according to the disclosed devices, kits and methods, which may be used in medical procedures, may be made of materials such as polyester (for example, DYNEEMA®), nylon or a suture. A thickness of a thread used to form a volute elongated hardened element according to the disclosed devices, kits and methods, which are used in medical procedures for joining soft tissues may range between 0.05 to 1.2 millimeter, 0.3 to 1.0 millimeters, 0.5 to 0.8 millimeters, 0.1 to 0.3 millimeters or 0.8 to 1.2 millimeters. A thickness of a thread used to form a volute elongated hardened element according to the disclosed devices, kits and methods used in medical procedures for joining sclerous tissues may range between 0.5 to 5 millimeter, 1 to 4 millimeters, 2 to 3 millimeters, 0.5 to 2 millimeters or 3 to 5 millimeters. A length of an elongated hardened element according to the disclosed devices, kits and methods, which are used for meniscus repair, may range between 2 to 11 millimeter, 4 to 9 millimeters, 6 to 7 millimeters, 2 to 5 millimeters or 9 to 11 millimeters. A width of an elongated hardened element according to the disclosed devices, kits and methods, which are used for meniscus repair, may range between 0.5 to 3 millimeter, 1 to 2.5 millimeters, 1.5 to 2 millimeters, 0.5 to 1.5 millimeters or 2 to 3 millimeters.

Reference or description of one end portion of a flexible tube of the disclosed devices and kits, may also apply to the other end portion of the flexible tube.

The devices, kits and methods disclosed with respect to repairing of a meniscus tissue, may also apply to the devices, kits and methods for joining two elements, with the required modifications.

The disclosed devices and kits may be operated according to the disclosed methods.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device comprising:
   a flexible tube comprising a first collapsible end portion, a first end portion and a second end portion;
   a first actuating element segment secured to the first collapsible end portion and extending along the first collapsible end portion,
   wherein, when the first collapsible end portion is threaded through a first aperture and the first actuating element segment is pulled proximally, the first collapsible end portion collapses proximally and forms a bulge larger than the first aperture, thereby anchoring the flexible tube against a rim of the first aperture,
   wherein said first actuating element comprises a thread or a rigid roll, said first end portion comprises a first elongated hardened element, and said second end portion comprises a second elongated hardened element, wherein said second elongated hardened element is threaded on the said second end portion by a loop.

2. The device of claim 1, wherein said first elongated hardened element is located at a tip of the said first end portion.

3. The device of claim 1, wherein the first and second end portions are a tubular mesh.

4. A method for closing a gap between a first object and a second object, the method comprising:
   connecting the firt object and the second object with the device of claim 1, thereby closing a gap between the first object and the second object.

5. The method of claim 4, wherein said gap is a tear in meniscus tissue, said first object is a proximal wall of said meniscus tissue and said second object is a peripheral distal wall of said meniscus tissue.

6. The method of claim 5, further comprising puncturing the meniscus tissue, wherein puncturing the meniscus tissue is performed by two tubular needles of an applicator.

* * * * *